United States Patent
Steen et al.

(10) Patent No.: US 10,405,756 B2
(45) Date of Patent: Sep. 10, 2019

(54) AFTERLOAD DEVICE FOR A BEATING HEART DURING EXAMINATION THEREOF

(71) Applicant: XVIVO PERFUSION AB, Göteborg (SE)

(72) Inventors: Stig Steen, Lund (SE); Audrius Paskevicius, Lund (SE); Benjamin King, Takaka (NZ)

(73) Assignee: XVIVO PERFUSION AB, Göteborg (SE)

(*) Notice: Subject to any disclaimer, the term of this patent is extended or adjusted under 35 U.S.C. 154(b) by 431 days.

(21) Appl. No.: 15/031,640

(22) PCT Filed: Oct. 24, 2014

(86) PCT No.: PCT/SE2014/000127
§ 371 (c)(1),
(2) Date: Apr. 22, 2016

(87) PCT Pub. No.: WO2015/060762
PCT Pub. Date: Apr. 30, 2015

(65) Prior Publication Data
US 2016/0262634 A1    Sep. 15, 2016

(30) Foreign Application Priority Data
Oct. 24, 2013  (SE) .................................... 1330132

(51) Int. Cl.
*A61B 5/02*     (2006.01)
*A01N 1/02*     (2006.01)
(Continued)

(52) U.S. Cl.
CPC ........ *A61B 5/02028* (2013.01); *A01N 1/0247* (2013.01); *A61B 5/0215* (2013.01);
(Continued)

(58) Field of Classification Search
CPC .............. A61B 5/02028; A61B 5/6876; A61B 5/02158; A61B 5/0215; A61B 5/02233;
(Continued)

(56) References Cited

U.S. PATENT DOCUMENTS 4,627,419 A * 12/1986 Hills .................... A61M 1/1065
128/DIG. 12
4,906,229 A *  3/1990 Wampler ............ A61M 1/1098
128/DIG. 3
(Continued)

FOREIGN PATENT DOCUMENTS

WO        2009136838 A1     5/2009

OTHER PUBLICATIONS

Westerhof, et al., "The Arterial Windkessel," Med Biol Eng Comput, 2009, vol. 47, pp. 131-141.
(Continued)

*Primary Examiner* — Liban M Hassan
(74) *Attorney, Agent, or Firm* — Pearne & Gordon LLP

(57) ABSTRACT

An examination device for a heart. An afterload device connected to the aorta provides a counter-pressure by an annular space delimited between a rigid cylinder and an elastic tube inserted in the rigid cylinder. The annular space comprises a compressible medium, such as air, nitrogen gas or carbon dioxide and is connected to a reservoir providing a predetermined pressure corresponding to a diastolic pressure. The reservoir is connected to the annular space via a restriction and a back-flow valve. During diastole, the annular space is inflated by the reservoir and provides a diastolic counter pressure for providing coronary flow. During systole, the ejected fluid from the heart ventricle displaces the medium inside the annular space through the restriction to the reservoir, thereby removing energy from the fluid. The compressible medium forms a compliance. Also, there is a
(Continued)

preload device comprising a vertical collapsible tube for preload of the atrium.

12 Claims, 14 Drawing Sheets

(51) Int. Cl.
| | |
|---|---|
| *A61B 5/00* | (2006.01) |
| *A61B 5/0215* | (2006.01) |
| *A61B 5/022* | (2006.01) |
| *A61B 5/023* | (2006.01) |
| *G09B 23/30* | (2006.01) |

(52) U.S. Cl.
CPC ...... *A61B 5/02158* (2013.01); *A61B 5/02233* (2013.01); *A61B 5/6876* (2013.01); *A61B 5/023* (2013.01); *A61B 2505/05* (2013.01); *G09B 23/306* (2013.01)

(58) Field of Classification Search
CPC .... A61B 5/023; A61N 1/0247; G09B 23/023; G09B 23/306
USPC ...................................................... 435/284.1
See application file for complete search history.

(56) References Cited

U.S. PATENT DOCUMENTS

| | | |
|---|---|---|
| 5,336,051 A | 8/1994 | Tamari |
| 6,443,884 B1 * | 9/2002 | Miyawaki ........... A61M 1/1086 600/17 |
| 7,045,279 B1 | 5/2006 | Laske |
| 2003/0073912 A1 | 4/2003 | Melvin |
| 2005/0147958 A1 | 7/2005 | Hassanein |
| 2007/0098694 A1 | 5/2007 | Khuri |
| 2007/0275364 A1 | 11/2007 | Hassanein |

OTHER PUBLICATIONS

Knowlton, et al., "The Influence of Variations in Temperature and Blood-Pressure on the Performance of the Isolated Mammalian Heart," Journal of Physiology, 1912, vol. 44, pp. 206-219.

Fisher, et al., "A Controllable Artificial Afterload for Isolated Heart Studies," Journal of Biomedical Engineering, 1984, vol. 6, pp. 305-310.

Hansen, et al. "Longitudinal and Radial Distensibility of the Porcine Aortic Root," The Annals of Thoracic Surgery, 1995, vol. 60, pp. S384-S390.

Kaetzel, et al., "Annexin VI Regulation of Cardiac Function," Biochemical and Biophysical Research Communications, 2004, vol. 322, pp. 1171-1177.

Lankhaar, et al., "Quantification of Right Ventricular Afterload in Patients with and without Pulmonary Hypertension," Am. J. Physiol. Heart Circ. Physiol., 2006, vol. 291, pp. H1731-H1737.

Katz, et al., "The Action of Digitalis on the Isolated Heart," American Heart Journal, 1938, vol. 16, pp. 149-158.

Seifen, et al., "Comparison of Cardiac Effects of Enflurane, Isoflurane, and Halothane in the Dog Heart-Lung Preparation," Journal of Cardiothoracic Anesthesia, 1987, vol. 1, pp. 543-553.

* cited by examiner

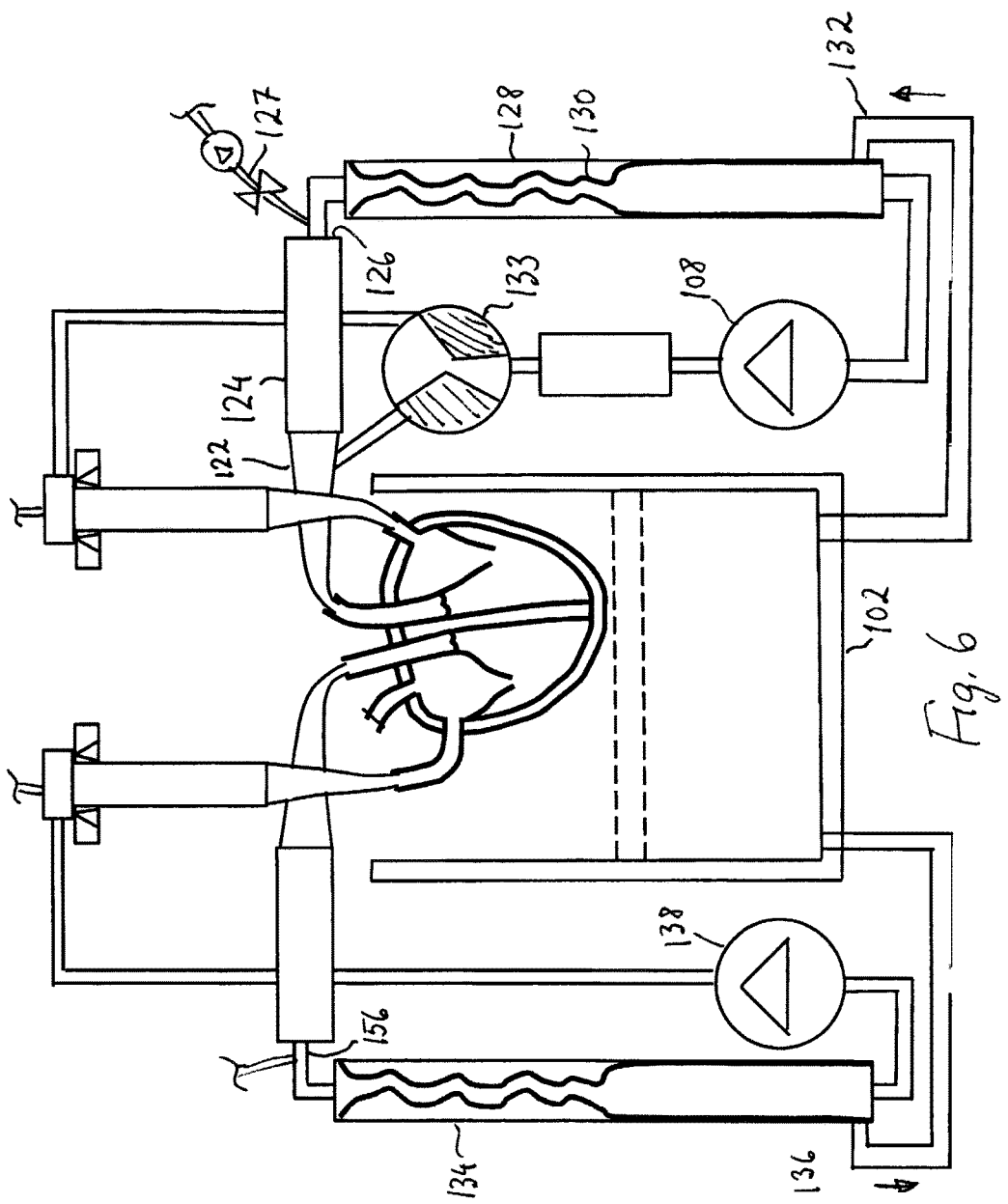

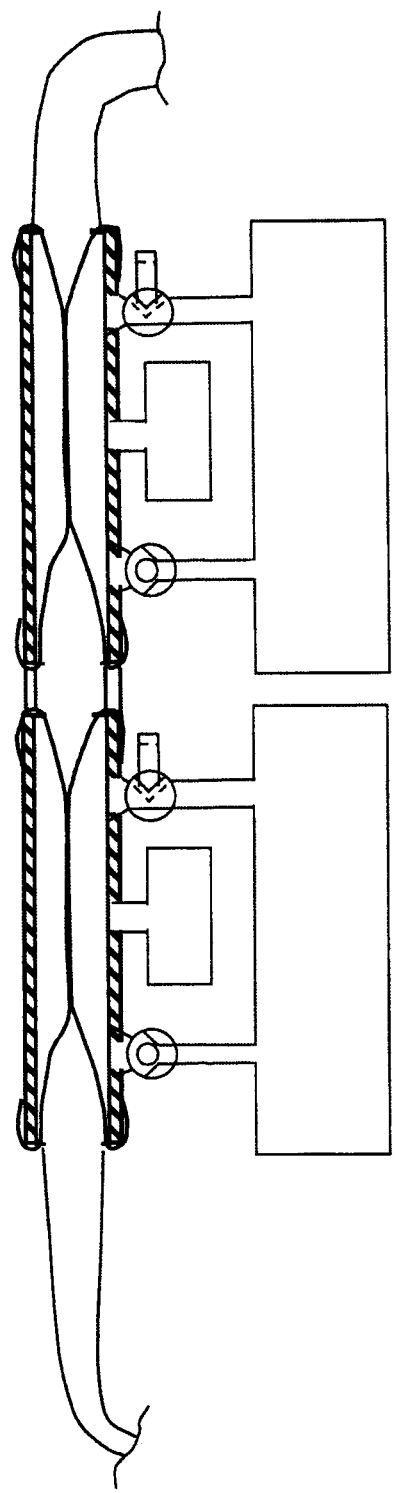

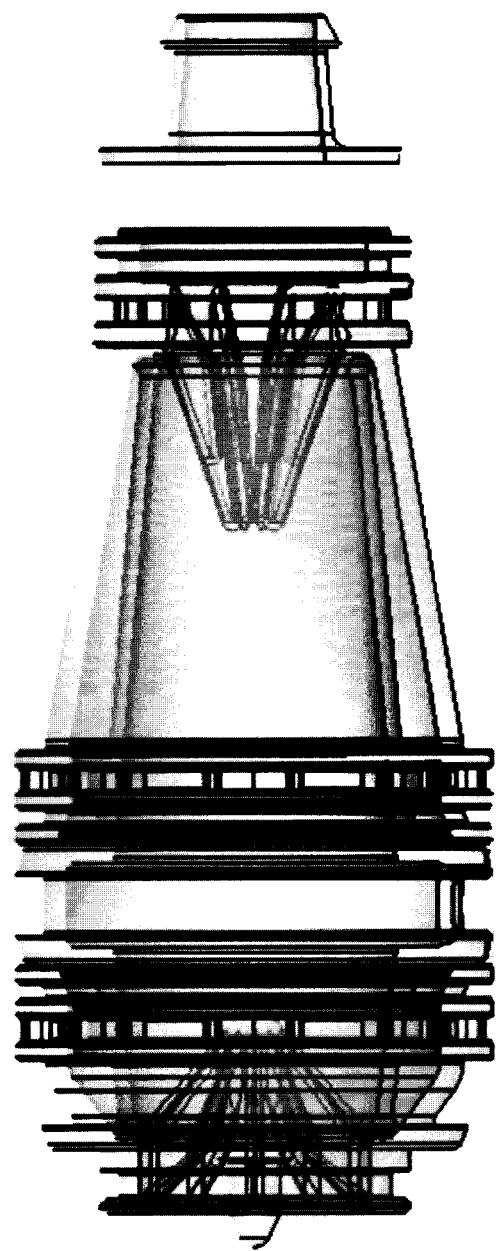
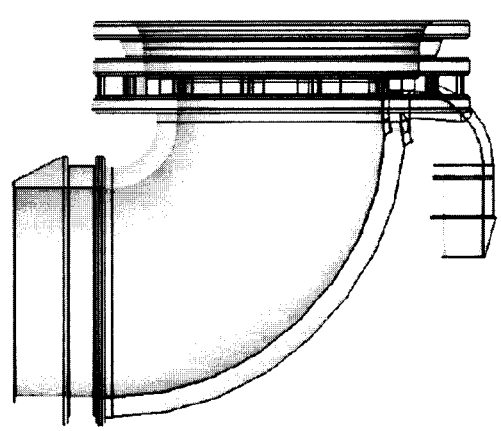
Fig. 11

AFTERLOAD DEVICE FOR A BEATING HEART DURING EXAMINATION THEREOF

FIELD OF INVENTION

The present invention relates to a method and device for organ examination, specifically when the organ is the heart.

BACKGROUND OF THE INVENTION

In an article published in 1912 with the title: "The influence of variations in temperature and blood-pressure on the performance of the isolated mammalian heart", by F. P. Knowlton and E. H. Starling, from the Institute of Physiology, University College, London, there is disclosed a method by which it is possible to determine the output of the left ventricle under approximately normal conditions, and to vary at will the arterial resistance, the venous pressure, the filling of the heart, or the temperature of the blood supply to the heart. This device is the basis for many later developed afterload devices for determining the output of the heart.

In another article with the title: "The arterial Windkessel" by Nico Westerhof, Jan-Willem Lankhaar and Berend E. Westerhof, published in 2008, a lumped model of a so-called Windkessel model is disclosed.

As discussed in more detail below, the previously known devices have a number of drawbacks, the most striking being that they cannot allow the heart to produce a normal diastole. If the isolated heart model is used as described, no proper heart function is obtained.

Thus, there is a need for a better afterload device, which does not load the heart with a large volume of fluid. In addition, there is a need for a preload device, in which the risk of including air into the fluid flow is minimized or removed. In addition, numerous other improvements are required.

SUMMARY OF THE INVENTION

Accordingly, an object of the present invention is to mitigate, alleviate or eliminate one or more of the above-identified deficiencies and disadvantages singly or in any combination.

Thus, there is provided an afterload device according to the present invention, which imitates the afterload of the heart produced by the body itself. In particular, there is provided a desired resistance towards the flow and a desired compliance together with a small inertial load. A preload device is provided, in which introduction of air in the fluid flow is removed.

According to a first aspect, there is provided an afterload device for a beating heart during examination thereof, whereby the heart is provided with a fluid flow to a left or right atrium of the heart and the afterload device is connected to a left or right ventricle of the heart, said afterload comprising: an inertia device comprising a tube connected to the ventricle and enclosing a fluid volume providing an inertia; a compliance device arranged after the tube and providing a compliance, said compliance device comprising a membrane being in contact with said fluid at one side and being in contact with a first medium volume at the other side; and a first restriction device arranged adjacent the membrane device and providing a resistance to the fluid flow. The afterload device comprises a second restriction device connected at one end to the first medium volume enclosed by said membrane and at another end to a second medium volume, for providing a medium flow resistance to medium flow from said first medium volume to said second medium volume.

In an embodiment, a backflow valve may be connected in parallel with said second restriction device and arranged to prevent flow from said first medium volume to said second medium volume and allow flow from said second medium volume to said first medium volume, whereby the pressure in said first medium volume will always be equal or larger than the pressure in said second medium volume. The medium may be a compressible medium, such as gas, and that the pressure in said second medium volume is maintained at a pressure, which corresponds to a desired systolic pressure. The gas may be any one of air, nitrogen gas, carbon dioxide gas, argon, vapour and any combinations thereof.

In another embodiment, the first restriction device is a dynamic flow restriction device having large resistance at low flow and small resistance during high flow during one and the same heart beat. The compliance device may further comprise: a rigid body and a membrane tube arranged inside the rigid body for forming an annular space between said rigid body and said membrane tube defining said first medium volume; whereby fluid provided by the heart during systole via the first tube displaces said medium inside said annular space via the restriction to the second medium volume, whereupon a medium resistance is provided towards the fluid flow during systole and a retrograde fluid flow is provided during diastole for providing coronary flow.

An adjustable volume may be connected to said first medium volume in order to form an adjustable compliance. There may be arranged a valve for switching between a retrograde perfusion of the aorta and a normal perfusion of the aorta.

In a further embodiment, the afterload device may comprise vanes arranged adjacent an inlet of the annular space for keeping an entrance thereof open and vanes arranged adjacent an outlet of the annular space for keeping an outlet thereof open.

The first restriction device may comprise a central plug and annular slits, which are covered by said membrane device at the start of systole for providing a large resistance, and whereby the slits are uncovered during the systole for decreasing the resistance, during a single heart beat.

The afterload device may be used together with a preload device comprising a flexible and collapsible cylindrical tube arranged substantially vertically and which is filled with fluid at a desired flow rate, whereby a fluid column is created in the bottom of the collapsible cylindrical tube and whereby the tube above the fluid column is collapsed, whereby an atmospheric pressure is generated above the fluid column, whereby a predetermined load pressure is provided to fill the atrium. The preload device may further comprise a de-aeration device for removing possible air inside the collapsible tube.

BRIEF DESCRIPTION OF THE DRAWINGS

Further objects, features and advantages of the invention will become apparent from the following detailed description of embodiments of the invention with reference to the drawings, in which:

FIG. 6 is a schematic view similar to FIG. 5 of an alternative circulation system embodiment of the invention.

FIG. 8d is a schematic view similar to FIG. 3a showing still another embodiment of the afterload device.

FIG. 11 is a drawing of the afterload device corresponding to the embodiment according to FIG. 9.

DETAILED DESCRIPTION OF EMBODIMENTS

Figure 1:
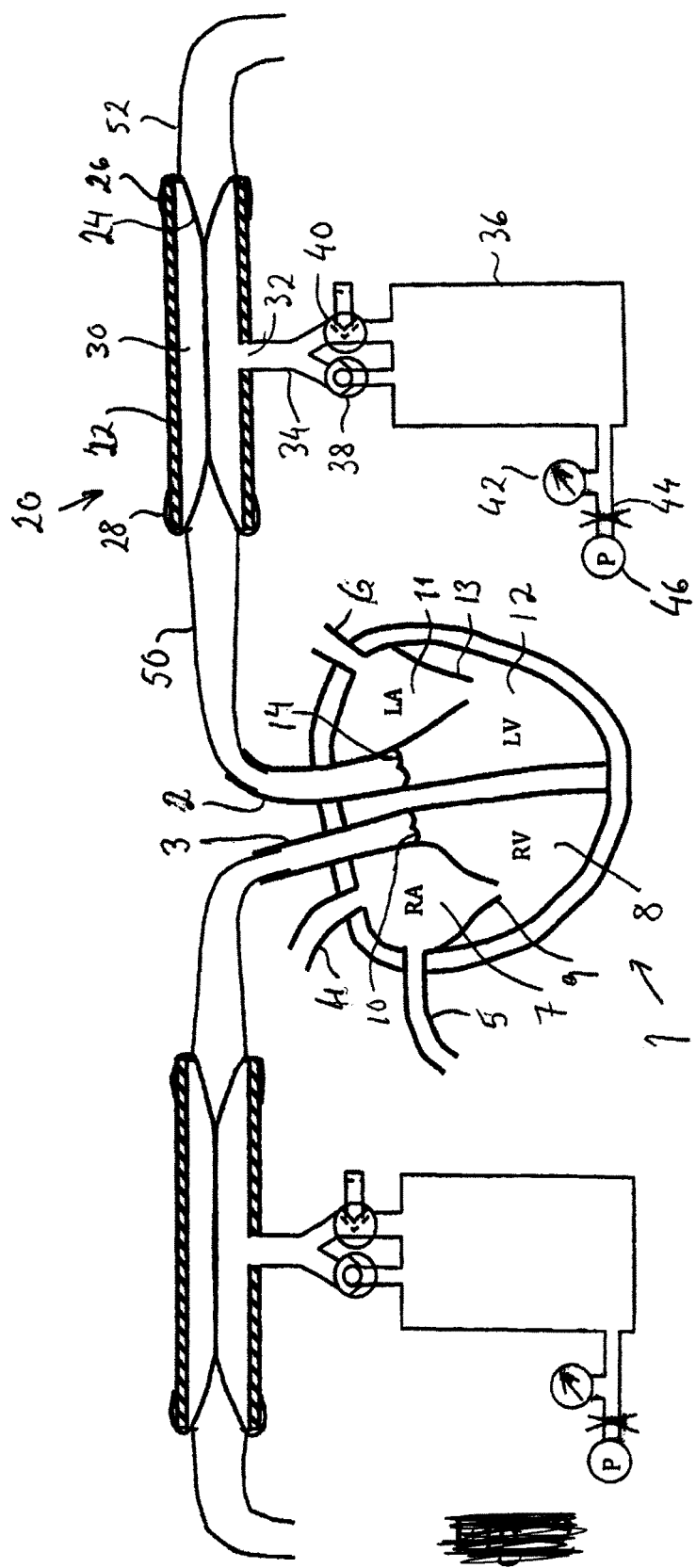
FIG. 1 is a schematic view partially in cross-section of afterload devices according to a first embodiment of the invention connected to the two ventricles of the heart.

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

In devices known from U.S. Pat. No. 7,045,279, it is common to connect the aorta of the heart to an afterload container via a tube. The afterload container is maintained at a height above the heart to provide a diastolic pressure of for example about 70 mmHg. The diameter of the tube should be in the same order of size as the aorta, for example about 25 mm. Thus, the volume of fluid in the tube may be almost 0.5 liters. When the heart contracts at the start of the systole, the left ventricle first contracts in an isovolumetric ventricular contraction, during which the aortic valve is closed. When the pressure inside the left ventricle has increased to that beyond the aortic valve, i.e. 70 mmHg, the aortic valve opens and the left ventricle starts to eject the fluid. However, the water column of about 500 ml in the tube now becomes superimposed on the contents of the left ventricle, which may be about 130 ml. Thus, the left ventricle must accelerate the entire fluid column in the tube, which takes some time, because of the considerable inertia of the fluid column. Thus, the ventricular and aortic pressures rise, but the ejection rate is slow. There will be a discontinuity in the pressure curve at the opening of the aortic valve. This will cause an overload of the left ventricle, which may extend the volume of the left ventricle and in the end may cause left ventricular congestion.

When the left ventricle stops to contract, the fluid column has a certain flow velocity upwards. Because of the high inertia of the fluid column, the flow cannot immediately be reversed, but the flow continues upward for a time period, during which a negative pressure is developed inside the left ventricle. During this time, further fluid is ejected out of the left ventricle. During this phase, the negative pressure inside the left ventricle is unphysiological and may cause problems and may propagate to the atrium, which is undesirable.

After the velocity of the fluid column has returned to zero, a reversal of the flow takes place, whereupon the aortic valve closes. The high inertia and weight of the fluid column will now influence upon the aortic valve, which is exposed to high forces in order to stop the reverse flow, which may cause aortic valve problems.

If the flow in the tube is high, the diastolic pressure will not be established, but the heart is exposed to a lower diastolic pressure, which results in an inferior flow in the coronary artery, which is compromised.

Thus, it is evident that the fluid column in the tube exposes the left ventricle and aortic valve to forces that do not occur in the normal body.

In the natural position of the heart in the body, the compliance is provided by the aorta and this compliance is provided much closer to the left ventricle compared to the afterload chamber as mentioned above. The inertia of the fluid acting on the left ventricle during ejection in the body is much smaller than the fluid column of the tube. The resistance of the body is provided by the arterioles and the capillaries, and this resistance is higher than the frictional forces against the tube. In fact, the aorta and the blood vessels acts as a load similar to a distributed element model or transmission line model, which is well-known in the electrical system theory. The Windkessel model is an attempt to adapt the physiology to a lumped element model, which is more simple to construct.

Thus, there is a need of an afterload device that is able to more closely mimic the body response to left and right ventricular operations. A compliance is required close to the outlet of the ventricle. In addition, the fluid volume before the compliance should be relatively small, smaller than the volume of the ventricle, or even smaller than the ejection fraction, which is normally about 50 ml, see further below. Moreover, a certain resistance should be provided. In addition, the parameters should be able to be adjusted, so that the left ventricle and aortic valve are exposed to substantially similar pressure response from the afterload device as in the normal body and so that different load situations can be simulated. In addition, the right ventricle and pulmonary valve may be provided with a similar afterload device as the left ventricle.

There is also a need for a preload device, which does not introduce air, and which is able to more closely mimic the body operation, for both the left atrium and the right atrium.

In addition, there is a need for an afterload device, which provides the same diastolic counterpressure and the same initial resistance for each heart beat, and irrespectively of the flow rate. In this manner, the conditions the heart is exposed to will be standardized and the same for every heart beat.

It is generally recognized that in order to control a process, the control system should have a faster response characteristic than the system to be controlled. Normally, the control system should be at least ten times faster than the controlled system. In the present context, this translates to the fact that a medium, which is used to provide ventricular afterload should have ten times faster response time compared to the fluid in the heart itself. Such a fast response time cannot be provided by a liquid column, since it has too high inertia. Thus a medium having at least ten times lower inertia should be contemplated. Such a medium is for example a gas, such as air, carbon dioxide or nitrogen gas. Below, air will be used as an example.

The present embodiments comprises an afterload device connected to the aorta that provides a counterpressure by an annular space delimited between a rigid cylinder and an elastic tube inserted in the rigid cylinder. The annular space comprises a compressible medium, such as air, nitrogen gas or carbon dioxide and is connected to a reservoir providing a predetermined pressure corresponding to a diastolic pressure. The reservoir is connected to the annular space via a restriction and a back-flow valve. During diastole, the annular space is inflated by the reservoir and provides a diastolic counterpressure for providing coronary flow. During systole, the ejected fluid from the heart ventricle displaces the medium inside the annular space through the restriction to the reservoir, thereby removing energy from the fluid. The compressible medium forms a compliance.

In addition, the present embodiments comprises a preload device comprising a vertical collapsible tube forming a fluid column for preload of the atrium with a desired preload pressure without introducing air into the fluid. A pump delivers fluid to the preload device and removes fluid from the afterload device.

FIG. 1 shows an afterload device according to a first embodiment of the invention, connected to the leftover of the aorta after the heart has been harvested. The heart is still beating.

The heart is shown partially schematic in cross-section. It is traditional in textbooks to show the heart "inverted" so that the left atrium and left ventricle are shown to the right and the right atrium and right ventricle are shown to the left on the drawing.

The heart 1 is during harvesting cut from the corresponding arteries and veins. Thus, there is provided leftovers of the aorta 2, the pulmonary artery 3, the superior vena cava 4, the inferior vena cava 5 and the pulmonary veins 6. For simplicity, a reference below to the aorta 2 means the leftover of the aorta after the heart has been harvested, and the same for the other vessels mentioned above.

In the system according to embodiments of the invention the flow of fluid is approximately as follows.

The fluid is introduced into the right atrium 7 via a separately formed opening (not shown) provided in the ausiculium between the superior and inferior vena cava. In this manner, the right atrium opening will be positioned in line with and opposite to the tricuspid valves. The inferior vena cava 5 and the superior vena cava 4 may be closed by sutures. The fluid is moved further to the right ventricle 8 via the tricuspid valve 9 in order to fill both the right atrium 7 and the right ventricle 8. At contraction of the right atrium followed by contraction of the right ventricle 8, fluid is expelled through pulmonary artery 3, whereupon the pulmonary valve 10 is opened.

At the left side of the heart, fluid, which is oxygenated, is introduced into the left atrium 11 via a separately formed opening (not shown) arranged in line with and opposite to the mitral valve. The fluid is moved further to the left ventricle 12 via mitral valve 13 in order to fill both the left atrium 11 and the left ventricle 12. At contraction of the left atrium 11 followed by contraction of the left ventricle 12, fluid is expelled through the aorta 2, whereupon the aortic valve 14 is opened.

In addition, a coronary flow is provided, see further below.

The left and right circulation systems may each comprise an afterload device for providing the heart with an afterload which closely mimics the afterload of a normal body.

In an embodiment of the afterload device 20 as shown in FIG. 1, the afterload device 20 comprises a rigid tube 22, which may be cylindrical and has an inner diameter corresponding to the diameter of a conventional aorta or slightly larger. The length of the tube may be sufficient for enclosing an ejection volume of the left ventricle, which may be for example 50 ml. The afterload device is arranged substantially horizontally. The rigid tube may have a rectangular shape or triangular shape.

Inside the rigid tube 22 is arranged an elastic or flexible tube 24 having substantially the same inner diameter as the rigid tube and being slightly longer than the rigid tube. The elastic tube 24 is at both ends 26, 28 folded backwards over the rim of the rigid tube and to the outer side of the rigid tube. The elastic tube ends 26, 28 are sealed to the rim or outer surface of the rigid tube, so that a closed annular space 30 is provided between the inner surface of the rigid tube 22 and the elastic tube 24.

The rigid tube 22 is provided with a side opening 32 connecting the annular space 30 with a control tube 34. The control tube 34 is connected to a large reservoir 36 via a one-way valve 38 and a restriction valve 40, arranged in parallel. The reservoir is provided with a pressure meter 42 for indicating the pressure inside the reservoir 36 and a connection tube 44 to a source of pressure 46, which may be air, carbon dioxide gas or nitrogen gas or another gas or medium, as will be discussed below.

The reservoir 36, the control tube 34 and the annular space 30 is provided with the medium at a desired pressure, for example corresponding to a desired diastolic pressure of the heart, such as 60 mmHg. The medium pressure will inflate the elastic tube 24 so that the elastic tube 24 will substantially fill and close the inner space of the rigid tube 22, as shown in FIG. 1.

The back-flow valve 38 is arranged in such a position that flow of medium from the reservoir 36 to the annular space takes place unimpeded. However, a flow from the annular space 30 to the reservoir 36 cannot take place via the back-flow valve 38 but has to pass through the restriction valve 40.

The rigid tube 22 is at one side provided with a tube connection piece 50, which at its other end is connected to the aorta 2 outlet of the heart. The rigid tube 22 is at its other end provided with an outlet tube 52, which opens into a fluid reservoir (not shown).

Between the rigid tube 22 and the outlet tube 52 there is arranged a flow restriction device 54, which comprises a central plug 56 and a number of slits 58 arranged along the radius from the plug to the periphery of the flow restriction device. The flexible tube 24 covers the slits in the start position, when there is no flow as shown in FIG. 1.

The afterload device 20 operates in the following manner, with reference to FIGS. 2a to 2d.

1) During the first isovolumetric ventricular contraction, the aortic valve 14 is closed and the space from the aortic valve, via the tube 50 up to the closure of the annular space 30 is filled with fluid, such as blood or an evaluation or examination fluid. The fluid in the tube 50 is at a diastolic pressure corresponding the inside pressure of the annular space 30, such as 60 mmHg.

Figure 2A:
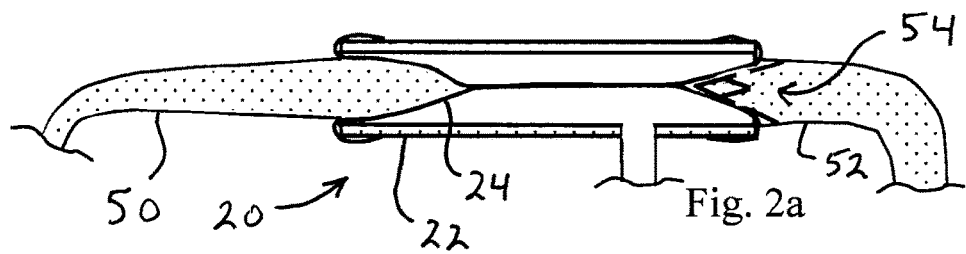
FIGS. 2a, 2b, 2c and 2d are cross-sectional views of the afterload device according to FIG. 2 in sequential positions during a heart beat.

2) When the pressure inside the left ventricle has increased to slightly above the diastolic pressure, the aortic valve 14 opens and the volume of fluid inside the left ventricle, which may be about 120 ml, is connected to the volume of fluid inside the tube 50, which may be about 15 ml, as shown in FIG. 2*a*. Thus, the left ventricle operates against a inertial load corresponding to about 135 ml, which is close to the situation in the normal body. The inertial load determines the very initial pressure increase rate in the left ventricle and tube 50. The inertial load should be adjusted so that there is substantially no discontinuity in the pressure curve of the left ventricle. This inertial load is adapted by changing the volume of the tube 50 as discussed below.

Figure 2B:
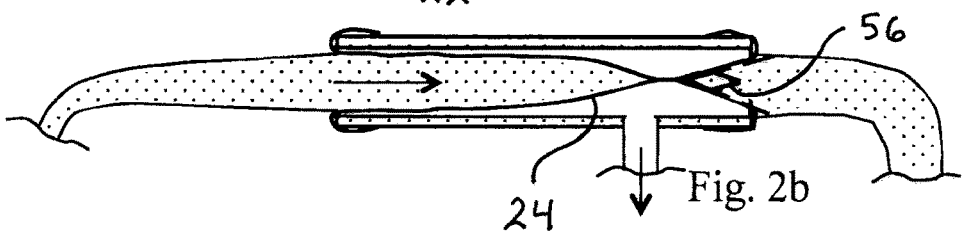

3) After opening of the aortic valves, the fluid volume of the left ventricle is expelled and the volume of fluid inside tube 50 is accelerated and moved inside the interior of the elastic tube 24, as shown in FIG. 2*b*. During this movement, the volume of medium inside the annular space 30 and inside the tube 34 forms a compliance, the size of which depends on the volume of the annular chamber 30 and the tube 34. This compliance can be adjusted, for example by changing the volume of the tube 34, as further described below.

4) The fluid volume inside tube 50 is moved into the inside of the elastic tube 24, thereby deflating the annular space 30 and the pressure inside the annular chamber 30 increases as the fluid in tube 50 displaces the medium inside the annular chamber. This pressure increase will add to the pressure increase initially caused by the inertia of the fluid and result in the fact that the top pressure of the left ventricle is increased, as in the normal body. There will be developed a gas pressure difference from the tube 34 to the reservoir 36, which will cause gas medium to flow from tube 34 via restriction 40 to the reservoir 36. During this medium flow through the restriction 40, a resistance is provided, which consumes energy from the blood. The resistance is adjustable by adjusting the opening size of the restriction valve 40. The resistance of the restriction 40 together with the capacitance of the annular space 30 and the inductance of the volume of fluid in the tube 50 and the ventricle will form a well defined load on the heart, which determines the pressure increase per time of the heart ventricle, which is an important parameter to measure. Since there is only gas between the annular space 30 and the restriction 40 there is no (or small) inertia added to the inertia of the fluid in the tube.

5) When a portion of the ejection volume has been passed out of the ventricle, the fluid inside the annular chamber 30 reaches the end, where a flow restriction device 54 is arranged. The flow restriction device is initially closed by a centrally arranged flow plug 56. When the flexible tube 24 is moved by the flow, a portion of the radial slits 58 are uncovered and allow flow through the restriction device. The more the flexible tube 24 uncovers the radial slits 58, the less resistance towards the flow is exerted by the restriction device.

Figure 2C:
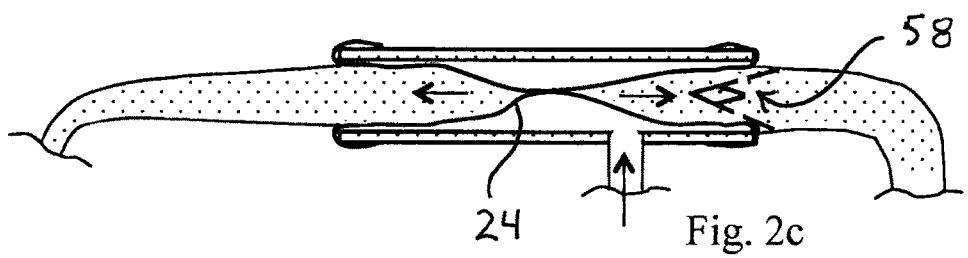

5) After the top pressure has been obtained, the flow of fluid inside the elastic tube will be decelerated and finally reversed. When the pressure inside the annular chamber 30 has dropped to the desired diastolic pressure prevailing inside the reservoir 36, a further decrease of pressure in the annular space 30 is prevented by a flow of gas medium through the back-flow valve 38 into the tube 34 and to the annular space 30. A portion of the fluid is expelled to the right and out through tube 52 and another portion of the fluid is expelled to the left, thereby closing the aortic valves. This operation is shown in FIG. 2*c*.

Figure 2D:
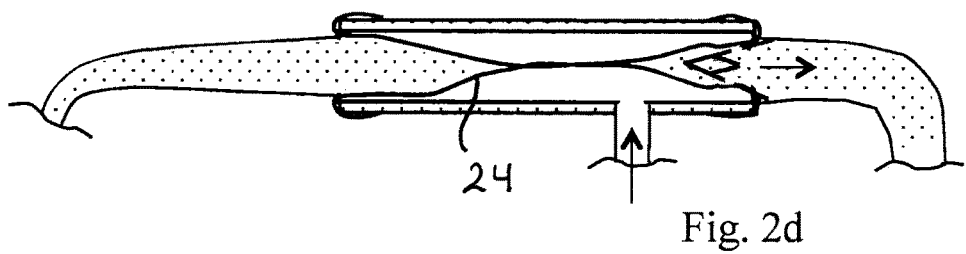

6) The pressure in tube 50 is now close to the desired diastolic pressure, which prevails inside reservoir 36. A coronary flow is developed, which is about 5 ml during the diastole per heart beat. This situation is shown in FIG. 2*d*. After the diastole, the situation is again as shown in FIG. 3*a*.

Thus, the afterload device 20 provides an inertia (inductance), a compliance (capacitance) and a resistance, which mimic the condition in a normal body and which are adjustable.

Since all parameters are adjustable, the same afterload device can be used for the right ventricle, whereupon the tube 50' is connected to the pulmonary artery instead of the aorta, as shown in FIG. 1. In this case, the pressure inside the reservoir is adjusted to for example 10 mmHg and the resistance is decreased compared to the situation at the left side of the heart.

Figure 3:
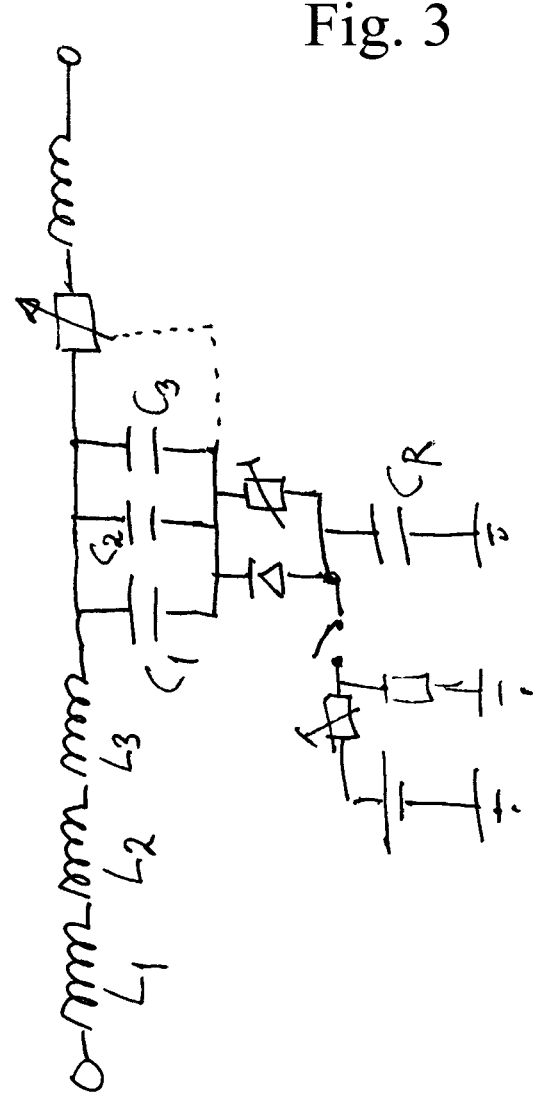
FIG. 3 is an electric diagram corresponding to the circulation system according to embodiments of the invention.

The afterload device may be illustrated as an electric scheme, in which the inertia is an inductor, the compliance is a capacitor and the restriction is an electric resistance, see FIG. 3.

The volume of fluid in the left ventricle and the volume of fluid in the tube 50 forms an inertial load corresponding to an inductor having an inductance L. The inductance may be divided in three portions, a first inductance L1 corresponding to the after-systole volume of the left ventricle, such as 75 ml, a second inductance L2 corresponding to the ejection fraction, such as 50 ml, and a third inductance corresponding to the volume of the connection tube 50, such as 15 ml. Before a systole, the arterial valve is arranged between the second and third inductance. After a systole, the arterial valve is arranged between the first and the second inductance.

The compliance comprises the volume of medium in the annular space and may correspond to a capacitor C. The capacitor is also divided in three portions, a first capacitor C1 corresponding to the volume of medium inside the annular space 30, a second capacitor corresponding to the parasitic volume of the side opening 32 and the control tube 34 and a third capacitor corresponding to a possible adjustment volume of fluid, see further below. The three capacitors C1, C2 and C3 are connected in parallel and are connected to a large capacitor C4 by a resistor R and a diode D. The charge of the large capacitor C4 is controlled to a value corresponding to a desired diastolic pressure P, such as 60 mmHg. The size of the first capacitor C1 is changed during the systole. If the maximum volume of the annular chamber, as shown in FIG. 3*a*, is about 75 ml, and the ejection fraction is 50 ml, the volume of the annular chamber changes between 75 ml as shown in FIG. 3*a* and 25 ml as shown in FIG. 3*b*. The second capacitor should be as small as possible, such as less than 5 ml. If the third capacitor is adjusted to a value of 20 ml, the total volume of the medium chamber will be 100 ml before a systole and 50 ml at the mid-systole. Thus, the pressure inside the annular space and connected spaces will increase from 60 mmHg to a value determined by the adjusted resistance and the force, which the heart can develop. Then, a certain amount of medium will pass from the first, second and third capacitors to the fourth capacitor via resistance 40 corresponding to electric resistance R, which maintains the pressure at for example below 120 mmHg during the following movement of the ejection portion. By adjusting the resistance 40, a smaller or larger amount of medium will pass to the reservoir, resulting in higher or lower maximum pressure. If the heart cannot produce a sufficient force for generating a desired pressure, for example 160 mmHg, the ejection fraction will decrease and also the top pressure. The maximum pressure obtainable is dependent on the force that the heart is able to produce. See further below.

The compliance during the systole is determined by the annular space compliance, which corresponds to a gas volume of for example 100 ml. During the end of the systole, the back-flow valve opens, which means that the annular space 30 and the reservoir are interconnected. Thus, the compliance is determined by the combined volume of the annular space and the reservoir. If the reservoir is 1000 ml (or larger), the compliance is increased to the tenth-fold or more. Thus, the compliance does no longer restrict the back-flow of the fluid towards the heart and the coronary vessels, which means that the coronary vessels are properly supplied and that the diastolic pressure prevailing in the reservoir is transmitted to the tube 50 and the aortic root. Any tendency for the fluid pressure to drop below the adjusted diastolic pressure is effectively prevented, which is essential for proper coronary supply.

The volume of the annular space 30 should be sufficient for substantially accommodating an ejection volume of the heart, which may be about 50 ml. Thus, the annular space should be between 25 ml and 100 ml, such as between 60 ml and 80 ml, for example 75 ml. The annular space should be between 50% and 200% of the normal ejection fraction, such as between 100% and 140% of the ejection fraction, such as 120% of the ejection fraction. We believe that if the annular space is larger than the maximal ejection fraction of the heart, a good operation will be achieved. However, the annular space should not be larger than double of the maximal ejection fraction.

The inertial load can be adjusted by inserting a connection portion 50 having a larger or smaller volume. However, practical experiments have shown that the volume of the connection portion 50 should be small, such as 15 ml or smaller. However, a volume of up to 50 ml may be desired. This should be compared to the volume of an aorta, which is normally about 100 ml. Thus, the volume of the connection portion, or rather the volume of fluid from the aortic valve and up to the start of the annular space as shown in FIG. 2*a*, should be from 10% to 100% of the aortic volume. We believe that if said volume is smaller than the aortic volume, a good operation will be achieved.

The resistor may be embodied as a clamping device reducing the effective cross-sectional area of the corresponding tube portion, as shown in FIG. 1. If the resistor is small, a small systolic pressure will be obtained and if the resistor is large, a high systolic pressure is obtained. An advantage of having the resistor arranged in the gas flow line instead of in the fluid flow line is that the medium gas has many times lower inertia, up to 1000 times lower. Thus, the heart is not exposed to an additional inertial load during the first portion of the systole and the derivative of the force build-up of the heart can be determined accurately. In addition, the resistor consumes energy instead of consuming the energy in a fluid flow resistor. Thus, the erythrocytes are exposed to less shear stress.

Figure 4:
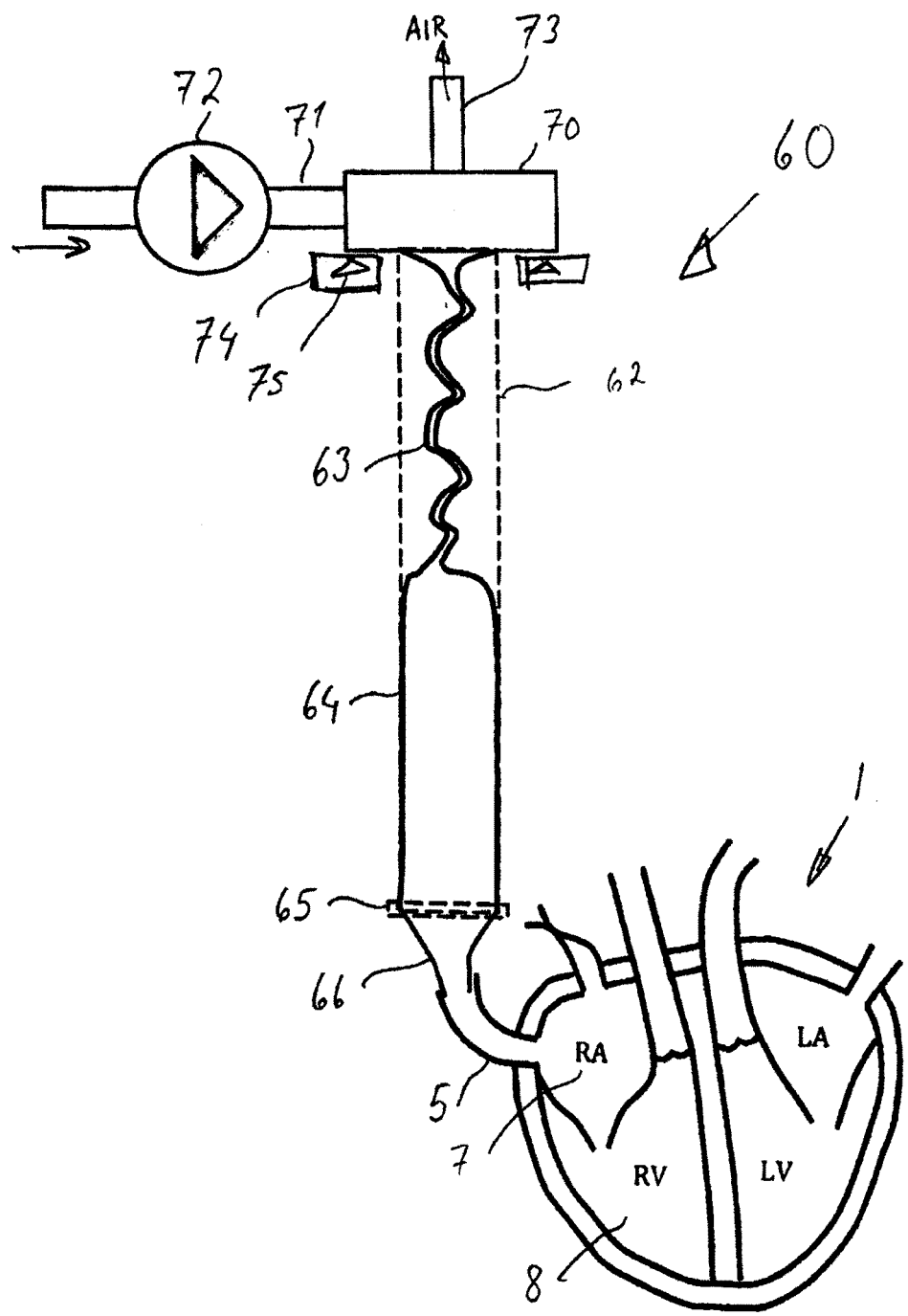
FIG. 4 is a schematic view of a preload device according to a first embodiment of the invention.

In another embodiment, the system comprises a preload device 60 shown in FIG. 4. The preload device 60 is connected to the inferior vena cava 5 in order to provide fluid to the right atrium 7 and the right ventricle 8. The fluid should be provided at a low pressure of about 5 mmHg.

The preload device comprises a substantially vertical cylinder 62 of a flexible but substantially non-elastic material as shown by broken lines in FIG. 4. The flexible material is sufficiently flexible for the material to collapse under a small overpressure, as shown in the upper part of the cylinder in FIG. 4. The lower part of the cylinder is filled with fluid, which extends the cylinder to its normal diameter. The diameter of the cylinder is larger than the normal diameter of the vena cava, which normally has a diameter of about 30 mm. The diameter of the cylinder in its extended diameter may be about 50 mm or even larger. If the diameter is 50 mm, the fluid level is lowered about 25 mm for a volume flow of 50 ml, which is a normal fill volume of the heart during diastole. The height of the fluid volume in the lower portion of the cylinder determines the filling pressure, which should be about 5 mmHg, which corresponds to a height of about 7 cm. The total height of the cylinder should be well larger than 7 cm, for example 14 cm or even 20 cm.

The lower portion of the cylinder 62 is connected to a flange 65. The flange 65 is connected to a connection tube 66 which is arranged at the inferior vena cava 5.

The upper portion of the cylinder 62 comprises a cylindrical housing 70. A fluid inlet tube 71 is connected to the side of the cylindrical housing 70 and offset from a radius thereof. The inlet tube 71 is connected to a pump 72, which provides fluid from a source (not shown). Thus, fluid is passed via pump 72 and the inlet tube 71 to the cylindrical housing 70 offset from the radius, whereby the inlet fluid flows in a circular path or swirl inside the cylindrical housing. Eventually, the fluid flows down the cylindrical housing and down into the flexible cylinder 62 connected there below.

A de-aeration tube 73 is connected to the center of the upper portion of the cylindrical housing 70. As shown in FIG. 4, the flexible material of the cylinder 62 collapses. The de-aeration operation is explained in further detail below. Any air inside the fluid is gathered in the center of the swirl and is sucked away via the de-aeration tube 73. Thus, the fluid is carefully de-aerated before being passed to the flexible cylinder and further to the right atrium of the heart. This is an important feature, since any air in the fluid may cause formation of micro bubbles and disturb the operation of the heart.

The cylindrical housing is supported at a desired height, by a support 74. The support may be provided with a load cell 75, as explained below.

Fluid is provided by the pump 72 at a constant rate as desired, for example 5 l/min, corresponding to 50 ml per heartbeat at a heart rate of 100 beats per minute. If the fluid column is about 70 mm, the right atrium and ventricle will be filled with a volume of 50 ml during the diastolic phase, which is about 70% of the heart cycle. Thus, the fluid level of the fluid column 64 will decrease some 15 mm during the filling phase. During the systole phase, there is no inflow of fluid into the right atrium (but a small reverse flow). Thus, the fluid column 64 will again increase to the start height of about 70 mm. Thus, the fluid column height will oscillate between 55 and 70 mm. If the pump is adjusted to a lower flow rate of for example 4 l/min, the level in the fluid column 64 will decrease. This will result in that the right atrium fills to a smaller degree with fluid, resulting in a smaller ejection volume. At the same time, the heart rate will automatically decrease somewhat in order to adjust the heart to the lower flow rate. Now, the fluid column 64 will stabilize at a lower level, for example at between 50 mm and 60 mm. The opposite will happen if the fluid flow rate is increased to for example 6 l/min.

If the heart encounters an atrial or ventricular fibrillation state, in which the right atrium and/or ventricle will not contract properly, the filling of the right atrium and right ventricle will be impaired. If the fluid pump 72 is operating at a high rate of for example 5 l/min, the upper flexible cylinder portion 63 will be filled with fluid in a few seconds, thus increasing the filling pressure of the right atrium. However, the weight of the flexible cylinder will increase when the fluid column 64 increases in size. Such an increase of weight can be sensed by the load cell 75. The load cell 75 can cause a computer to stop or retard the pump 72 and initiate a visual and/or sound alarm signal, in order to draw attention to the situation.

The preload device 60 has been shown in FIG. 4 connected to the right atrium. In addition or alternatively, another preload device may be connected to the left atrium.

Figure 5:
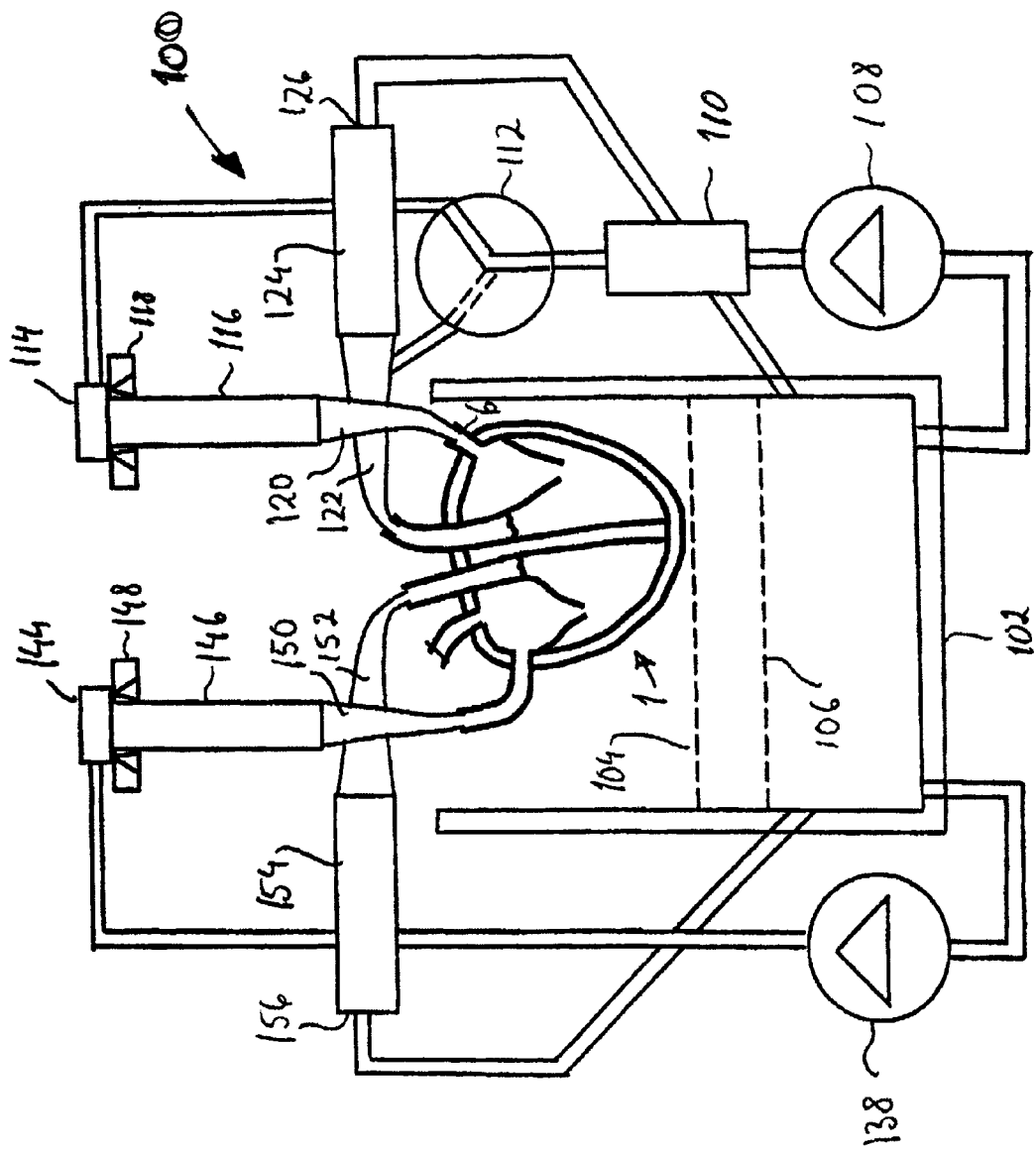
FIG. 5 is a schematic view of a complete circuit of a left circulation and right circulation system of the examination system according to an embodiment of the invention.

FIG. 5 discloses a first embodiment of a complete system 100 according to an embodiment of the invention. The same reference numerals have been used for the same components as in the previous figures. The heart 1 is arranged in a container 102 having a bottom wall 104, which is perforated. A fluid is arranged at the bottom of the container 102 as indicated by a fluid level 106. A left pump 108 for the left circulation circuit is arranged to the right of the container 102 and is connected to the bottom of the container for drawing fluid from the container. The left pump propels the fluid to an oxygenator 110 in which the fluid is oxygenated. From the oxygenator, the fluid passes to a switch valve 112, which during the "pump mode" shown in solid lines passes the fluid to the upper cylindrical housing 114 of a left preload device 116. The left preload device 116 is supported by a left load cell 118. The cylindrical housing is arranged substantially vertically and is at the bottom connected to the pulmonary vein 6 via a connection tube 120. During diastole, the fluid is introduced into the left atrium 11 and left ventricle 12. During systole, the heart contracts and expels fluid from the left ventricle 12 through the aortic valve 14 and aorta 2 to an inlet tube 122 of an afterload device 124. The outlet 126 of the afterload device is connected to the bottom of the container 102 in order to complete the left circulation circuit. The connections between the components are arranged by tubes of a suitable dimension, normally having an internal diameter of about 25 mm.

The switch valve 112 may be adjusted to the alternative position shown in broken lines, in which the fluid is passed from the valve 112 directly to the outlet tube 122, which is connected with the aorta, for retrograde circulation of fluid via the aorta to the coronary arteries, which are arranged slightly above the aortic valve. This alternative position is used during start-up of the system and when the heart is not pumping properly. The valve may be switched manually between the positions, but may alternatively be operated electronically, so that it may be controlled automatically be a computer in the system.

The right circulation system may have similar components, although the oxygenator and switch valve are not included in the right circulation system. A right pump 138 for the right circulation circuit is arranged to the left of the container 102 and is connected to the bottom of the container for drawing fluid from the container. The right pump propels the fluid to the upper cylindrical housing 144 of a right preload device 146. The right preload device 146 is supported by a right load cell 148. The cylindrical housing 144 is arranged substantially vertical and is at the bottom connected to the inferior vena cava 5 via a connection tube 150. During diastole, the fluid is introduced into the right atrium 7 and right ventricle 8. During systole, the heart contracts and expels fluid from the right ventricle 8 through the pulmonary valve 10 and the pulmonary artery 3 to an inlet tube 152 of an afterload device 154. The outlet 156 of the afterload device is connected to the bottom of the container 102 in order to complete the right circulation circuit. The connections between the components are arranged by tubes of a suitable dimension, normally having an internal diameter of about 25 mm.

The left pump 108 and the right pump 138 are independently adjusted to a desired flow rate, for example about 4 to 6 l/min. The flow rates do not need to be the same, since the two circuits are more or less independent from each other, the dependence being that the chambers of the heart beat in unison.

FIG. 6 shows another embodiment of the circulation systems. The circulation systems are similar to the embodiment of FIG. 5. However, the outlet tube 126 of the afterload device 124 of the left circulation circuit is provided with a collapsible device 128, which establishes atmospheric pressure immediately after the outlet 126 in order to avoid that a suction pressure is developed at the outlet 126. The collapsible device 128 is essentially equal to the preload device 146, but the swirl inlet may be included or left out, the latter being shown in FIG. 6, and comprises a flexible tube 130, which has a defined outer diameter, but can collapse to a smaller diameter. The bottom outlet from the collapsible device is connected directly to the inlet of the pump 108, whereby a closed left heart circulation circuit is provided. A separate tube 132 attached to the bottom of the collapsible device is connected to the reservoir 102 for providing extra fluid for compensating for the coronary flow, which leaves the left circulation circuit. The fluid, which is oxygenated by the oxygenator is not returned to the container 102 but only kept in the left circulation circuit. The coronary flow essentially passes from the aortic root immediately above the aortic valve to the right atrium.

A similar arrangement is made at the right circulation circuit, by means of a collapsible device 134 connected to the outlet 156. The bottom outlet from the collapsible device 134 is connected directly to the inlet of the pump 138, whereby a closed right heart circulation circuit is provided. A separate tube 136 attached to the bottom of the collapsible device 134 is connected to the reservoir 102 for removing fluid for compensating for the coronary flow, which is received by the right circulation circuit. The blood in the right circulation flow is not oxygenated, which is clearly visible through the transparent tubes of the right circulation system.

Thus, the flows in tube 132 and 136 each corresponds to the coronary flow. By measuring the flow in these two tubes and averaging the flow rates, the coronary flow can be measured. The coronary flow is normally about 5% of the left circulation flow. However, the flows in the tubes 132 and 136 also correspond to any leakage in the respective circuits.

FIG. 6 also includes a valve 133, which may be adjusted so that fluid passes to the inlet 122 for retrograde flow or that fluid passes to the preload device, as shown in FIG. 6. The valve 133 may also be adjusted so that the flow from the pump passes both ways for a short time duration, in order to remove air during startup of the system. In this manner, a smooth switch-over from retrograde to normal flow may be performed. The valve may be operated manually or by a computer.

Figure 7A:
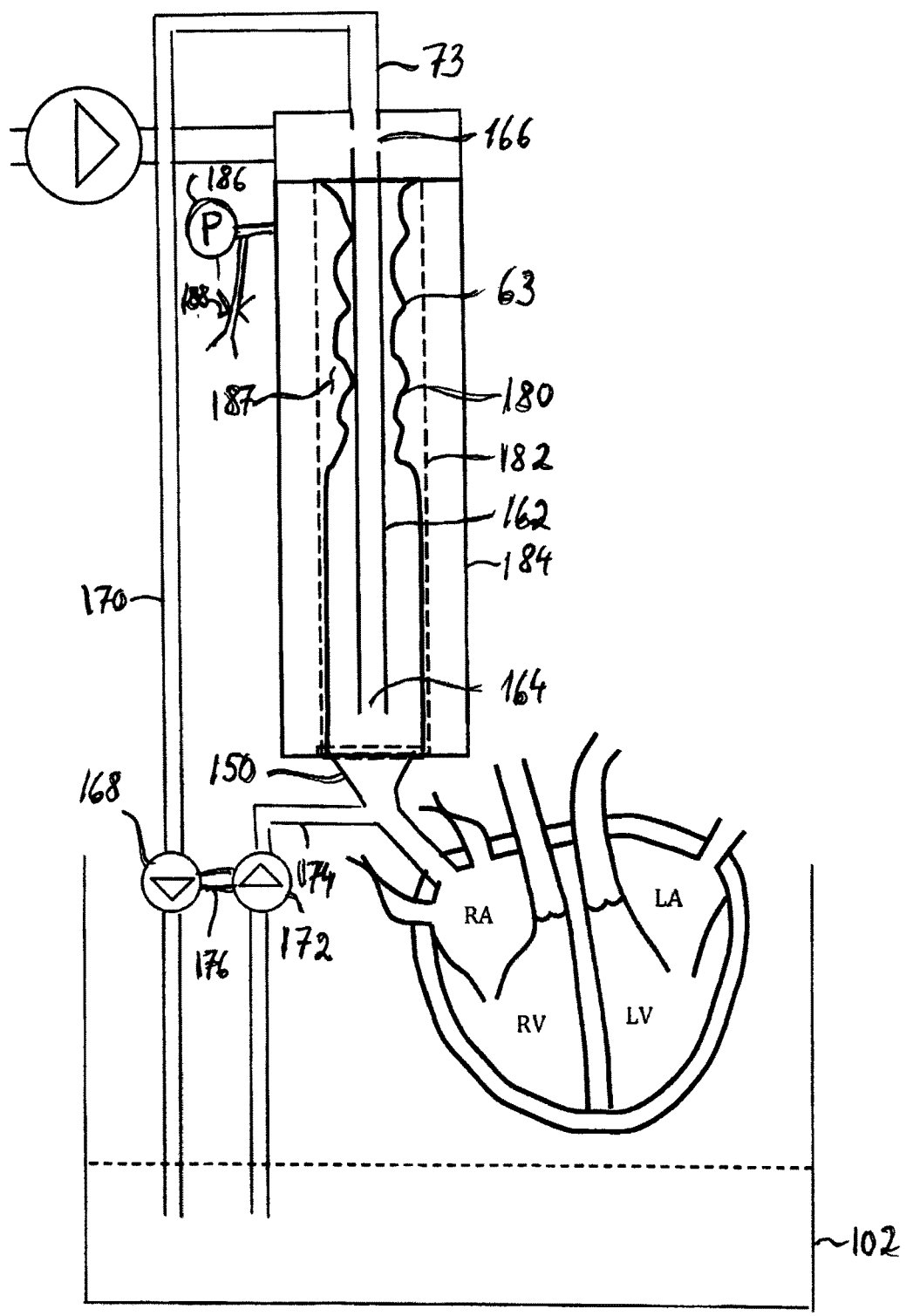
FIG. 7a is a schematic view of a preload device according to a second embodiment of the invention.
Figure 7B:
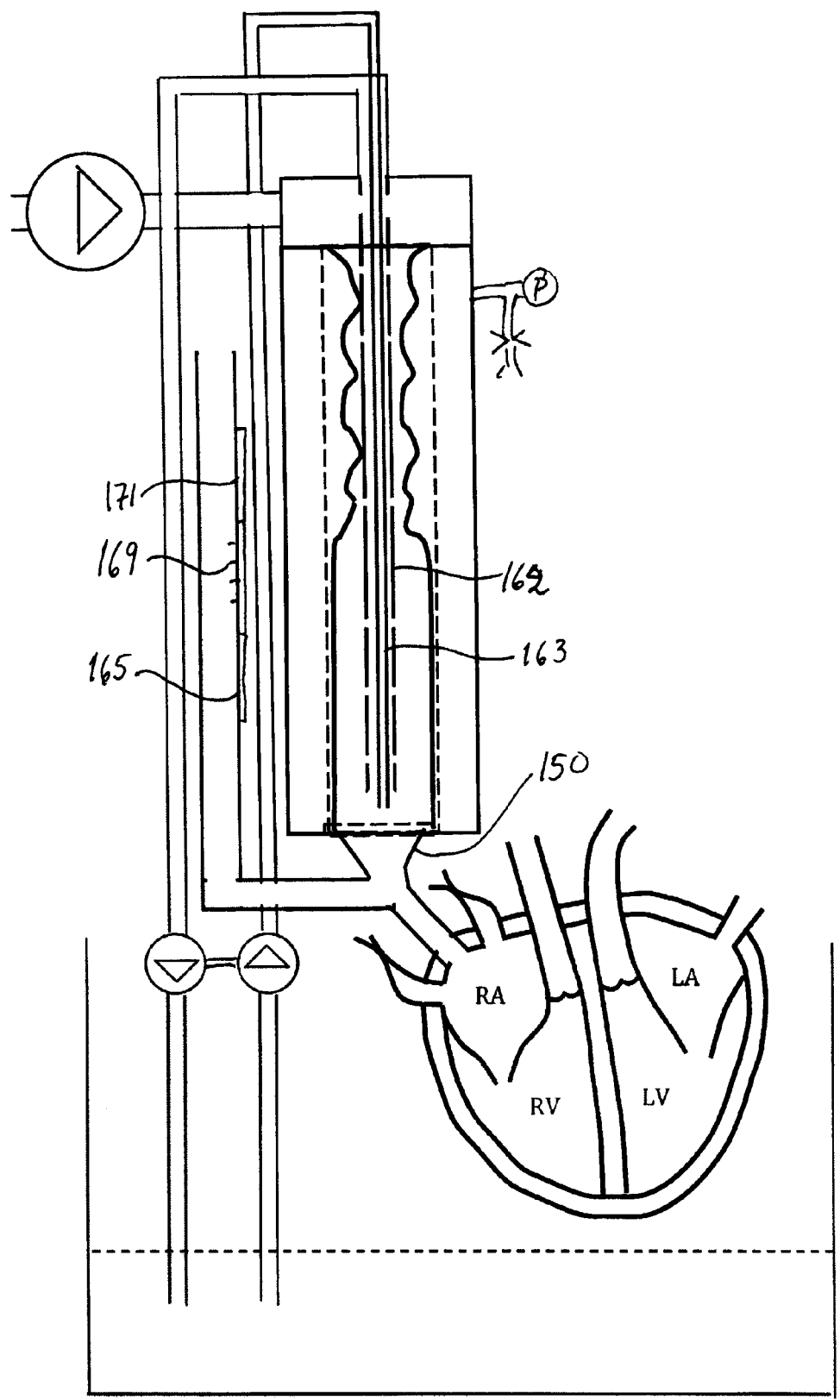
FIG. 7b is a schematic view of a preload device according to a third embodiment of the invention.

FIG. 7a discloses a further embodiment of the system, in which the de-aeration system shown in FIG. 4 is further explained. A de-aeration tube 162 extends all the way down inside the flexible cylinder portion 63 to adjacent the connection tube 150 to the right atrium of the heart. The bottom of the de-aeration tube 162 is open as indicated at 164. In addition, the de-aeration tube 162 is provided with openings 166 at least opposite to the swirl portion wherein fluid is introduced into the device. Additional openings may be provided along the length of the de-aeration tube 162. See FIG. 7b. The de-aeration tube 162 is connected to a pump 168 which pumps a mixture of air and liquid to the reservoir 102 via a tube 170. Another pump 172 pumps an equal amount of fluid from the reservoir 102 to the right circulation system, for example to the connection tube 150 as close as possible to the right atrium via a tube 174. The tube 174 may open at other positions in the right circulation system, such as adjacent the swirl device or as shown in FIG. 7b. The two pumps are interconnected so that they pump the same amount of fluid, as indicated by the lines 176. This may be accomplished by arranging the tubes 170 and 174 in the same peristaltic pump, in suitable directions. The first pump 168 removes any air inside the flexible cylinder portion 63 and in addition some fluid or liquid. However, every volume amount removed by first pump 168 is replaced by the same volume amount added by the second pump 172. Thus, it is ensured during operation that no air enters the right atrium. A similar de-aeration system is included in the left circulation system. In certain embodiments, the de-aeration system is only included in the left circulation system.

FIG. 7a also shows another embodiment of the flexible cylinder portion 63. The flexible cylinder portion 180 is surrounded by a rigid cylinder 182 which is perforated. The perforated cylinder 182 is surrounded by a closed cylinder 184. Thus, a closed and variable space 187 is provided between the closed cylinder 184 and the flexible portion 180. A pressure meter 186 is connected to the closed space. In addition, the closed space is connected to the atmosphere via a restriction 188. During normal operation, when there is substantially constant flow in the device, the pressure inside the closed space is the same as atmospheric pressure. However, if the heart stops to operate properly, for example due to fibrillation, the fluid rapidly accumulates in the flexible cylinder and inflates the flexible cylinder. This will cause an increase in the pressure inside the closed space 187, which may trigger an alarm and cause the pump to decrease the fluid flow. If the improper operation of the heart was temporary, the fluid level will return to the normal level and the operation can be continued. This is also sensed by the pressure meter, which may indicate to the system or a computer that normal operation can be resumed. An additional safety is obtained, since the flexible cylinder 180 will not be inflated excessively and the heart will not be exposed to large atrial pressure.

FIG. 7b discloses still another embodiment, in which the outlet from pump 172 passes via a tube 163 inside the interior of said tube 162 to the bottom of the preload device. A riser tube 165 is arranged connected to the outlet 150 so that the pressure in said outlet 150 causes the fluid in the riser tube to rise up to a level corresponding to the pressure in the outlet 150. A scale 169 is arranged for reading the pressure in for example cm waterpillar. An electronic sensor 171 may be arranged along the riser tube to sense and indicate the waterpillar level. If the pressure becomes too large, the riser tube will overflow to the reservoir positioned there below.

The two circulation systems are started up in the following steps, with reference to FIG. 5. In a first step, the valve 112 is switched to the alternative position shown by broken lines and a small flow is initiated, whereby the heart is provided with a retrograde flow at a very low pressure. The pressure may be so low that no actual flow takes place in the coronary vessels. The afterload device 124 is provided with no pressure in the annular space, which results in that fluid flows retrograde in the afterload device 124 and displaces all air inside the afterload device. The de-aeration device of the preload device 116 in the left circulation circuit is activated and removes air inside the preload device 116 and fills the preload device 116 with fluid by means of the pumps 168 and 172 shown in FIG. 7. There is a further de-aeration tube 127 (see FIG. 6) adjacent outlet 126 of the afterload device, which may be connected to a pump for removal of air. The same de-aeration pump may be used sequentially for the left circuit and for the right circuit.

The same sequence may be performed in the right circulation system, now or later. The fluid pump 108 is increased in speed so that oxygenated fluid passes retrograde into the coronary vessels. Then, the heart is defibrillated whereupon the switch 112 is moved to the normal position shown in solid lines. When the heart starts to operate, the speed of the pump 108 is increased until desired or normal operation is obtained. Then, the right circulation system pump 138 can be initiated.

Figure 8A:
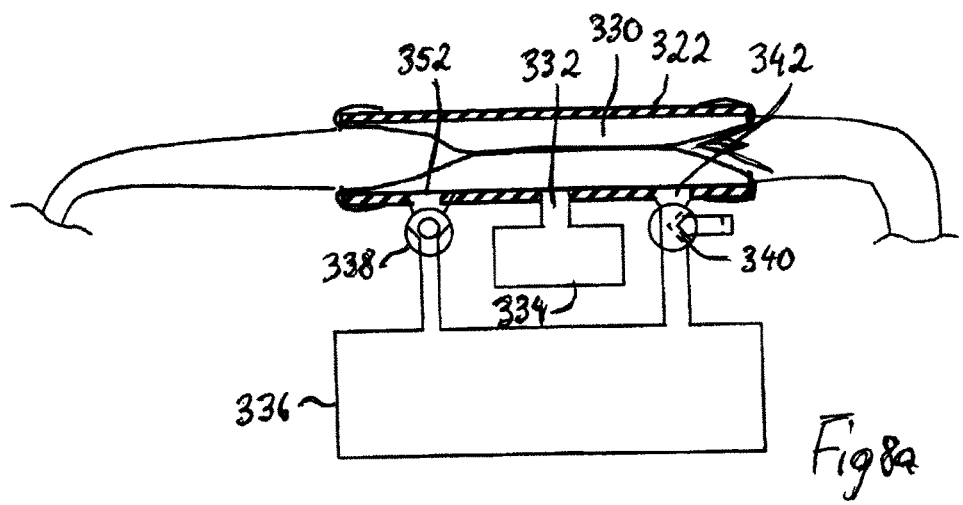
FIG. 8a is a schematic view similar to FIG. 3a showing another embodiment of the afterload device.

In another embodiment of the afterload device, the rigid tube is provided with a medium outlet adjacent the fluid flow outlet and a medium inlet adjacent the fluid flow inlet, as shown in FIG. 8a. The rigid tube 322 is provided with a first opening 332 substantially in the middle. The first opening opens into a space 334, the size of which is adjustable. This space corresponds to the capacitor C3 mentioned above. In addition, the rigid tube 322 comprises a second opening 342 to the right in FIG. 8a, which includes a restriction 340, similar to the restriction 40 described in FIG. 1. The rigid tube 322 is further provided with a third opening 352, which comprises a back-flow valve 338 similar to the one-way valve 38 in FIG. 1. The back-flow valve 338 and the restriction 340 are arranged very close to the rigid tube 322, so that the spaces between the rigid tube and the restriction 340 and back-flow valve 338 are as small as possible. These combined spaces correspond to the parasitic capacitor C2 mentioned before. In this embodiment, the parasitic volume can be made as small as 1 ml at each opening. Thus, the combined capacitance or compliance of the system can be adjusted by the volume 334 in combination with the annular space 330. The restriction 340 and the back-flow valve 338 are connected to a large space or reservoir 336, which is much larger than the annular space, for example more than 10 times larger. The operation is similar to that described above in connection with FIGS. 2a to 2d. However, the outflow of medium from the annular space to the reservoir via the restriction now takes place at the right side of the annular space, which means that the flexible tube is less likely to prevent or intervene at such flow. In addition, the flow of medium back from the reservoir to the annular space takes place at the left side of the annular space, resulting in a desired division of the fluid at a position opposite to the left opening 352, which will improve the operation. The inner surface of the rigid tube 322 may be provided with serrations, which prevents formation of entrapped medium pockets.

FIG. 8d shows that two afterload devices may be arranged in series, whereby each afterload device may be adjusted to different compliances and resistances. Three or more afterload devices may be arranged in series.

Figure 8B:
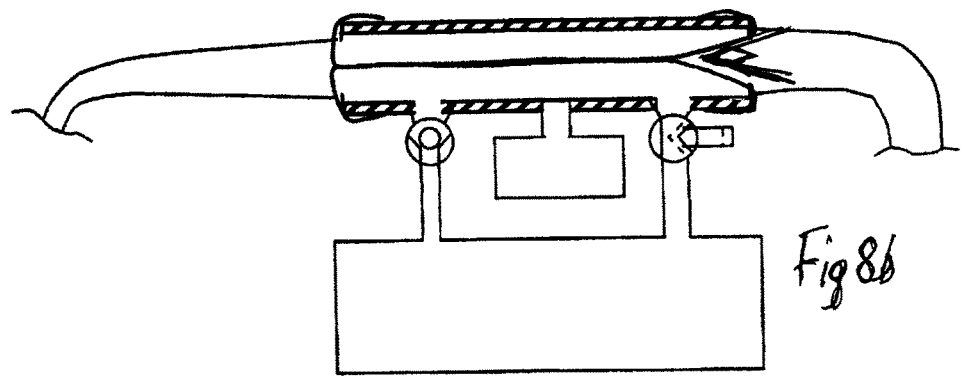
FIG. 8b is a schematic view similar to FIG. 3a showing undesired fluid flow features.

As shown in FIG. 8b, there is a risk that the left portion of the flexible tube bulges out to the left during the end of the diastole, due to the retrograde flow of the fluid into the coronary vessels. If this happens, there is a risk that the fluid at the start of the next systole will not be able to open the annular space and enter inside the annular space and flow to the left in FIG. 8b. This fact is seen as a reflection of a pressure wave coming from the ventricle and hitting an impedance change or gradient. The pressure wave will be reflected back to the ventricle and cause an unwanted pressure surge. Such operation can be seen on the ventricle pressure curve as a pressure disturbance shortly after the opening of the aortic valves. Such disturbance is larger at higher flows and pressures.

Figure 8C:
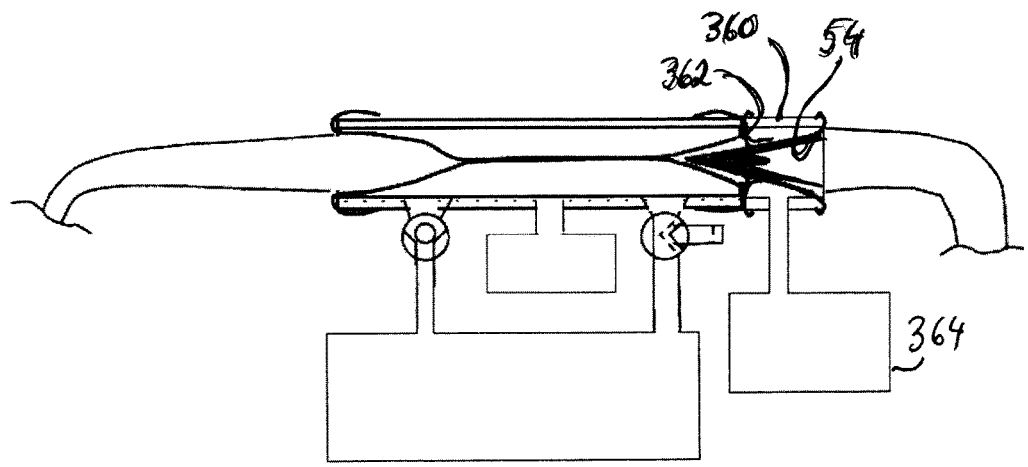
FIG. 8c is a schematic view similar to FIG. 3a showing still another embodiment of the afterload device.

FIG. 8c shows a device, in which the flow restriction device 54 is separated from the tube 24 in a separate device. A separate rigid tube 360 is arranged and encircling a flow restriction device 54 as shown in FIG. 2a. Inside the rigid tube 360, there is arranged a separate elastic or flexible tube 362, which is connected to a separate reservoir 364, which is maintained at a desired pressure, for example slightly larger than the diastolic pressure. The flexible tube 362 covers the slits 58 of the flow restriction device 54. The slits are opened when the pressure in the fluid flow exceeds the pressure in the reservoir 364 as indicated above.

In order to counteract such non-wanted operation, the rigid tube 322 may be provided with flanges or vanes preventing the nondesired bulging out of the annular tube at the left end and/or the right end. Such vanes are shown in the embodiment disclosed in FIG. 9.

Figure 9:
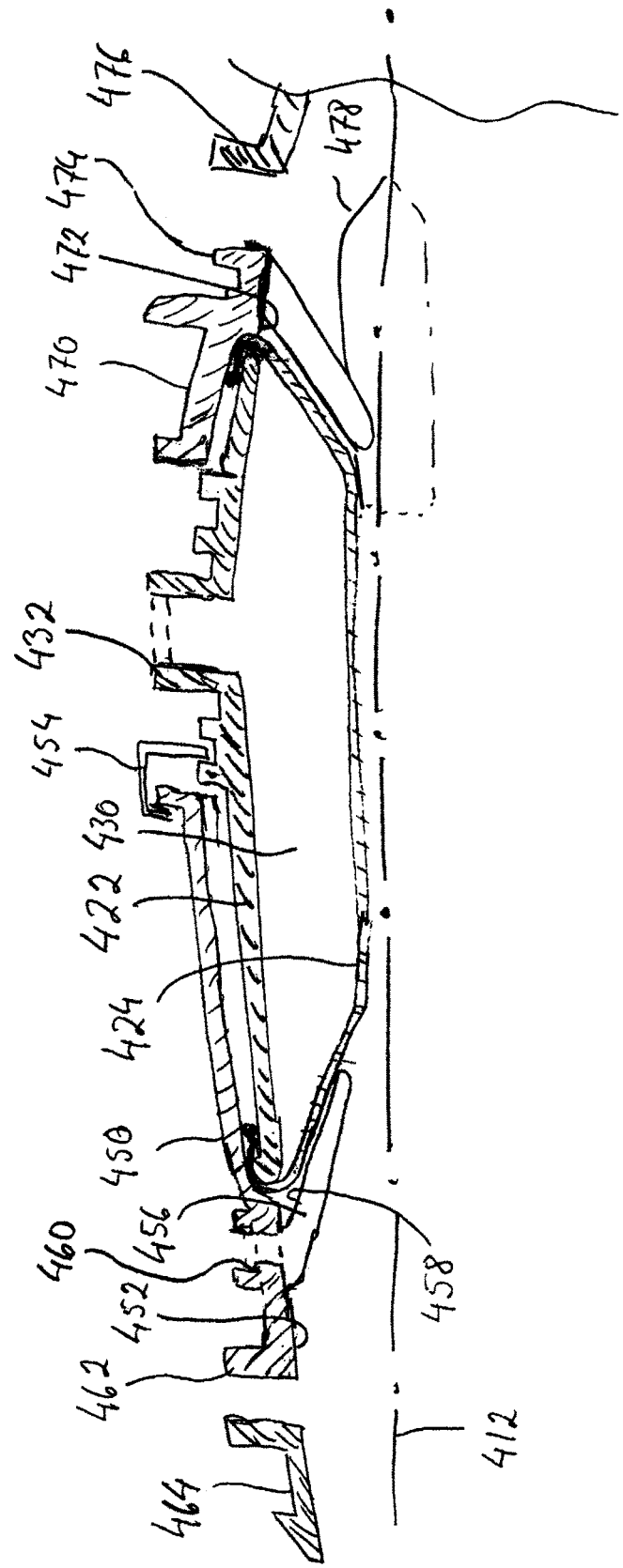
FIG. 9 is a cross-sectional view of yet another embodiment of the afterload device.

FIG. 9 shows another design of the afterload device, according to a further embodiment. The afterload device 400 comprises a central, substantially cylindrical body 422. The body is slightly conical whereby the inner surface forms an angle of about 5 degrees in relation to the symmetry axis 412. The entrance opening to the left has a diameter of about 25 mm and the diameter of the largest cross-section is about 35 mm. From the largest diameter in the middle, the cross-sectional diameter decreases to about 30 mm at the right outlet. The total length is about 100 mm. This gives a total inner volume of about 75 ml. An elastic or flexible tube 424 is arranged inside the cylindrical body 422 and is sealed at the rims of the cylindrical body so that a closed annular space 430 is formed between the inner surface of the cylindrical body 422 and the elastic tube 424.

The sealing is provided by a left connection portion 450 and a right connection portion 470. The inner surface 452 of the left connection portion 450 is arranged in line with the inner surface of the cylindrical portion and is an elongation to the left of the cylindrical body inner surface. Likewise, the inner surface 472 of the left connection portion 470 is arranged in line with the inner surface of the cylindrical portion and is an elongation to the right of the cylindrical body inner surface. The elongation is normally as short as possible, for example 10 to 15 mm.

As shown in FIG. 9, the flexible and/or elastic tube 424 is folded over the ends of the cylindrical body and squeezed between the rim of the cylindrical body and the respective connection portion. A clamp 454 connects the left connection portion 450 to the cylindrical body 422. The clamp may comprise some resiliency so that the connection portion 450 is urged to the left in relation to the cylindrical body. Similar clamps may be provided to interconnect the other portions of the afterload device.

The left connection portion 450 comprises several vanes 456. In the shown embodiment, there are eight vanes arranged peripherally. The outer surface 458 of the vanes form a conical surface, which is intermittent. The elastic tube is arranged to abut this outer conical surface when there is no counterpressure from a fluid, as shown in FIG. 9. Thus, the vanes prevent the elastic tube to bulge to the left, as illustrated in FIG. 8b. Likewise, the right connection portion 470 is provided with eight vanes forming an outer conical surface for support of the elastic tube 424 at the right side.

The left connection portion is provided with an opening 460 for introduction of fluid into the left connection portion during retrograde perfusion of the aorta, as described in connection with FIGS. 5 and 6. The right connection portion 470 may be provided with a similar opening (not shown) for removal of air during upstart of the procedure and also during the operation, should accumulation of air take place.

The left connection portion 450 comprises a flange 462 for connection to an inlet tube 464, which is connected to the pulmonary artery 3 or aorta 2. The inlet tube has an inner surface, which is arranged in line with the inner surface of the connection portion 450 so that no discontinuities are formed for the fluid flow. The inner surface of the inlet tube 464 may be slightly conical with an angle of 5 degrees. For hearts having smaller diameter aorta (women or children), the length of the inlet tube 464 is adjusted so that the aorta fits on the inlet tube 464. Alternatively, a children afterload device is used, having smaller dimensions.

The right connection portion 470 comprises a flange 474 for connection to an outlet tube 476, which is described below.

In the middle of the cylindrical body 422, there is arranged an opening 432 for connection of the annular space 430 to the reservoir via the restriction and the back-flow valve, as described in connection with FIG. 1. The opening may be arranged at any place along the cylindrical body 422, for example about 70% of the length from the left end as shown in FIG. 9. Alternatively, there may be two openings, as described in connection with FIG. 8a, one about 30% from the left end (for the back-flow) and one about 30% from the right end (for the resistance). Yet another opening may be arranged for connection to the adjustable space shown in FIG. 8a.

The inertial load on the heart ventricle may be adjusted by inserting or removal of one or several rings between the left connection portion 450 and the inlet tube 464. Such rings will increase the mass of the fluid from the aortic valve to the start of the elastic tube 424, which defines the inertial load (or inductance) of the ventricle. Another manner to increase the inertial load on the ventricle is to use a heavier gas as said medium, such as carbon dioxide.

The volume of the annular chamber 430 may be approximately equal to or larger than the ejection fraction of the ventricle. If the annular chamber is smaller than the ejection fraction, a flow path straight through the cylindrical body and the annular chamber may be generated at the end of the systole, i.e. that there are no portions of the elastic tube which contact each other in the center of the cylindrical body. Such straight flow path may not be detrimental if it occurs only during a short portion of the heart cycle. In addition, there is a central plug, preventing such flow.

In fact, the explanation of the flow as given with reference to FIGS. 2a to 2d is somewhat simplified and idealized, while the flow in reality is more stochastic.

However, it is expected that the afterload device will operate more reliably if the volume of the annular space is larger than the ejection fraction. Since the ejection fraction is varying, the annular space should be larger than about 140% of the normal ejection fraction. Such normal ejection fraction may be the ejection fraction of a heart operated at 5 liter per minute at a diastolic pressure of 80 mmHg and a systolic pressure of 120 mmHg. For a human heart, the normal ejection fraction is often defined as 50 ml. Thus, the annular space should be larger than 70 ml. In order to use the same device for any human heart, the annular space could be designed to be 75 ml, or at least between 60 ml and 150 ml.

The annular space 430 may be connected to an adjustable space 334 as described in FIG. 8a. In connection with parasitic spaces in the tubes and openings, the total volume inside the annular space and the adjustable space and the parasitic spaces may be adjustable from about 75 ml and up to about 200 ml, if the maximum volume of the adjustable space is about 110 ml. By adjusting the adjustable space, the compliance (capacitance) of the annular space will be adjusted. Thus, the influence of the compliance on the heart ventricle can be studied.

The fluid in the ventricle and in the space from the aortic valve and up to the left end of the elastic tube will form a fluid inertial body (L1+L2+L3), which interacts with the compliance with a time constant. The operation of this inertial body can be studied by stepwise inserting rings as indicated above, thereby stepwise increasing the portion of the inertial fluid body after the aortic valve (L3).

The annular space 430 is connected to a large reservoir of medium by a restriction device (resistance). Thus, the influence of such resistance to the heart and ventricle can be studied by varying the restriction.

The large reservoir is provided with medium at a pressure simulating the diastolic pressure. By varying the pressure in the reservoir, the heart may be subjected to different diastolic pressures.

The same afterload device can be provided at the left ventricle and the right ventricle, since the afterload device is adjustable to the conditions prevailing in the right heart circuit.

All pressures may be monitored and measured by pressure meters inserted at suitable locations, such as in the ventricle, shortly after the aortic valve and pulmonary valve, in the annular space, in the atriums and in the preload device. Optical fibers may be arranged for visualizing operation inside the heart. Temperatures may be measured at different places, etc. Such meters and sensors are not shown on the drawings as such are familiar to the skilled person. Examples are given in the prior art patent U.S. Pat. No. 7,045,279B1 mentioned above, and shown in FIG. 1.

Figure 10:
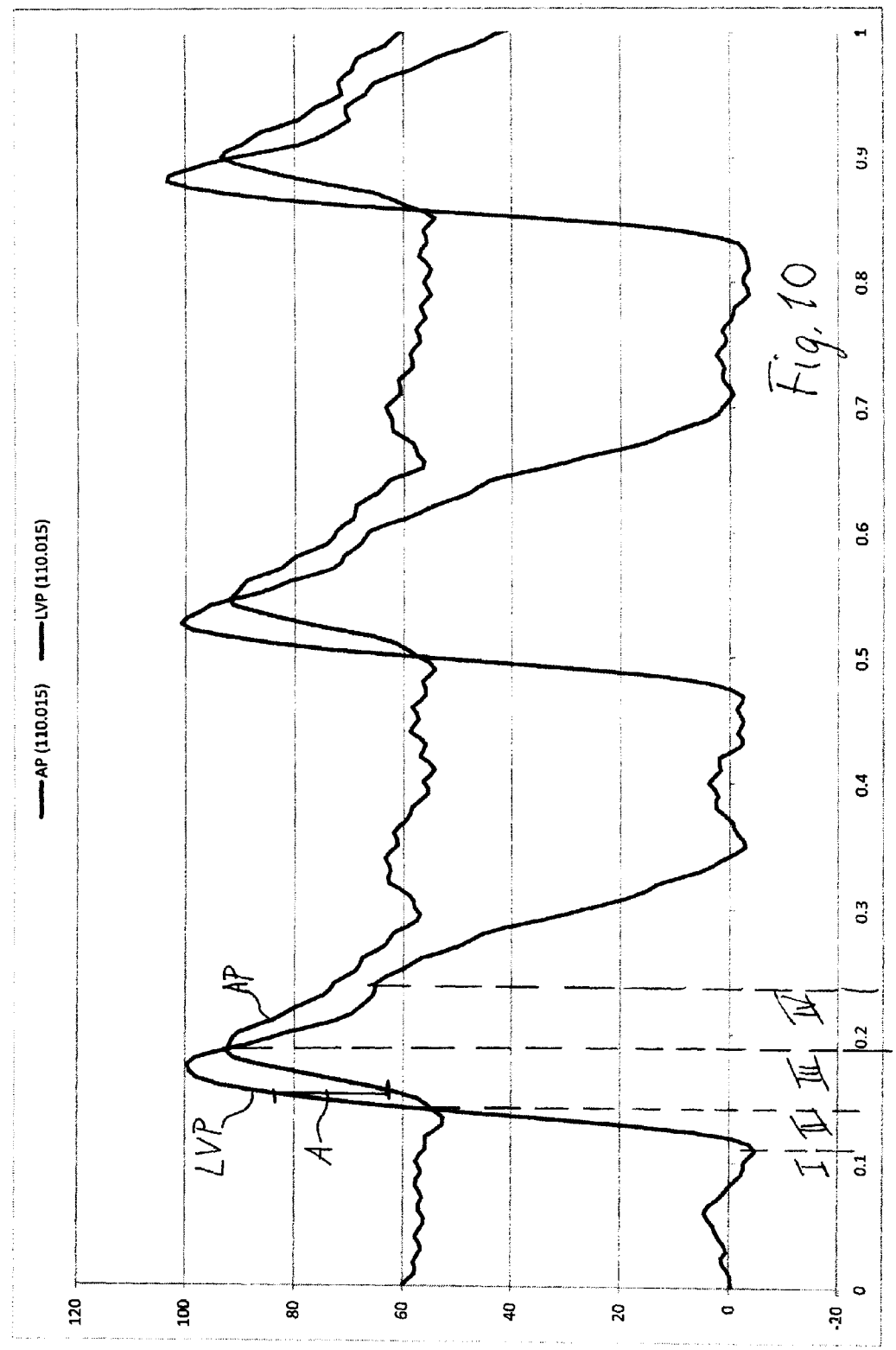
FIG. 10 is a pressure diagram showing the ventricular pressure and the pressure in an annular space in the afterload device.

Pressure curves for the pressure in the left ventricle and the pressure in the aorta are shown in FIG. 10. The diastolic pressure is set to 60 mmHg and a systolic pressure of 100 mmHg is obtained by adjusting the restriction. The flow is 6 L/min.

The left ventricular pressure is shown by solid line curve LVP and the pressure in the aorta is shown by the curve AP, which is close to the pressure in the annular space.

At time instant I, a systolic isovolumetric contraction starts.

At time instant II, the pressure in the left ventricle exceeds the diastolic pressure and the aortic valve opens. The pressure in the annular space increases. The above-mentioned fluid inertial body (L1+L2+L3) now accelerates at a rate determined by the difference between the LVP and AP curves. One such acceleration pressure is indicated by A in FIG. 10. The contraction force of the heart increases faster than the increase of pressure in the annular chamber. Thus, the fluid body is accelerated all the time. After a while, the heart muscle ceases to contract and the ventricular pressure is at maximum. However, the fluid has still a movement to the right in the annular chamber and the annular chamber pressure increases further for a short while.

At time instant III, the left ventricular pressure LVP decreases below the annular chamber pressure, whereby the fluid body starts to decelerate. The rate of deceleration is dependent on the difference between the annular chamber pressure and the ventricular pressure.

At time instant IV, the fluid body has been decelerated to zero speed, resulting in closure of the aortic valve and a rapid decrease of the left ventricular pressure to the diastole phase. The annular chamber still has a pressure higher than the diastolic pressure, probably dependent on the fact that the volume of fluid inside the annular chamber is divided in two portions, one to the left which provides antegrade flow to the coronary vessels and one to the right for expelling the fluid to the right of the afterload device. During this time, the back-flow valve passes medium from the reservoir to the annular chamber.

The influence of the compliance and resistance to the fluid body can be studied by adjustment of the different parameters. If the compliance is increased, the inclination of the heart pressure curve will be smaller, at least at the start of the systole.

If the resistance is lowered, the inclination of the curve at the end of period III will be smaller, which normally means that the peak LVP will be smaller. However, if the resistance is increased, the power of the heart may be insufficient for accelerating the fluid body, resulting in a smaller ejection fraction.

The closing time from the top pressure to the closure of the aortic valve is dependent on the time constant of the fluid body inertia and the compliance. If the compliance is small, the time will be larger, which may be suitable at the right circuit (pulmonary circuit). If the compliance is high (stiffer), the closing time is shorter.

Further interesting properties of the systolic action can be studied very much in detail by adjustment of the different parameters.

The diastolic action can be studied by adjusting the properties of the preload device. In particular, the filling pressure can be studied by studying the height of the water column in the preload cylinder. Since the aortic valve is closed, the afterload chamber would not influence particularly on the diastolic action.

The resistance of the restriction valve 40 determines the resistance during the first portion of the systole. During this time, the flow resistor 54 is closed. Thus, the restriction valve consumes all energy of the system. Some time after the start of the systole, the gas flow through restriction valve 40 stops, when there is no more compression of the annular space, and the flow restrictor 54 opens and takes over the energy consumption. Thus, the total resistance of the afterload device is determined by the restriction valve 40 during the initial portion of the systole and the total resistance of the afterload device is determined by the flow restrictor 54 during the rest of the systole. The flow restrictor 54 has a flow resistance which is adapted to the prevailing flow rate. However, the restriction valve 40 has a specific value which is the same at every start of a heart beat and in addition, the systole always starts from the same diastolic pressure as determined by the pressure in the reservoir. Thus, the heart is exposed to constant conditions during the first part of the systole which are the same for each consecutive heart beat.

FIG. 11 is a drawing of the afterload device shown in FIG. 9.

Figure 12:
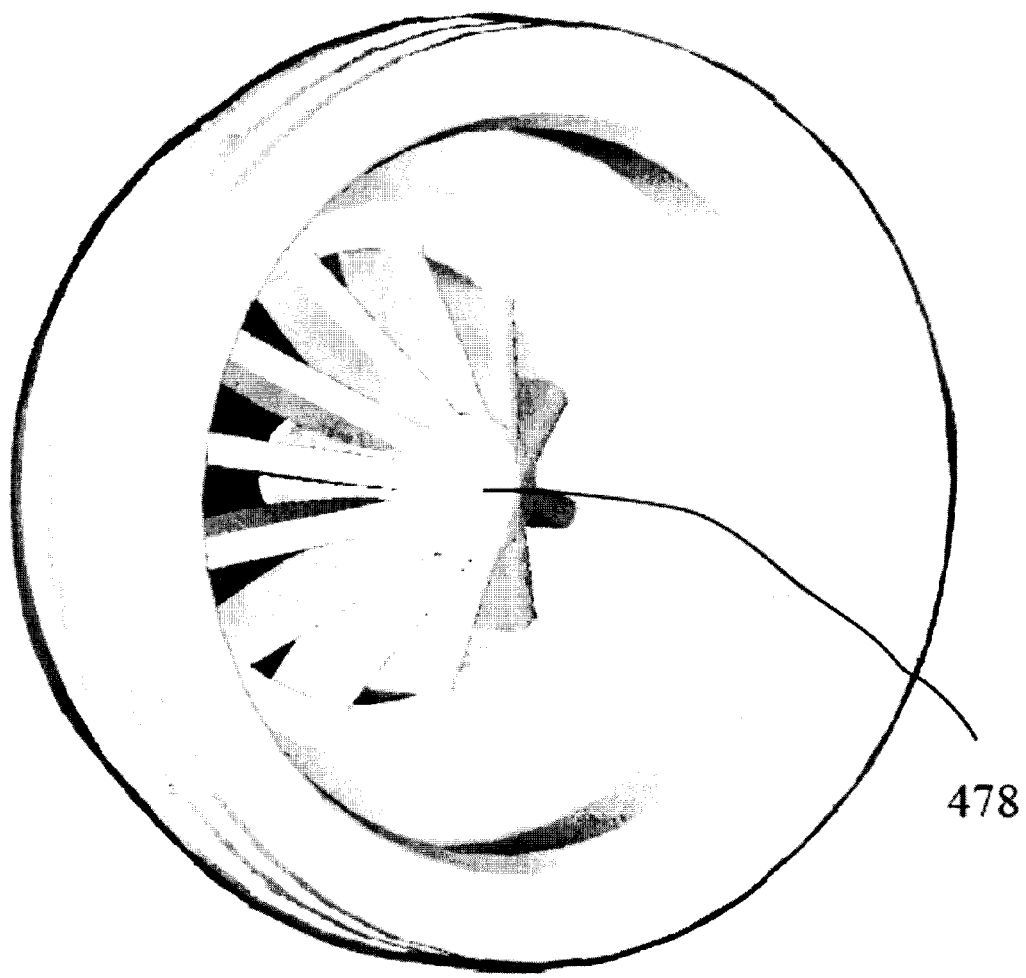
FIG. 12 is a perspective view of a connection portion comprising vanes and a central plug according to an embodiment of the afterload device.

FIG. 12 is a drawing of the right connection portion 470 in perspective showing the vanes. In addition, there is shown a central plug 478, which prevents flow through the center portion of the annular space, until the elastic tube has been moved from the conical surface of the vanes.

The outlet tube may be provided with a device causing the outlet flow to form a swirl and a direction change of 90°, similar to the inlet device of the cylindrical housing 70, as described above.

Normally, the afterload devices are arranged substantially horizontal, but a slight angle upwards in the flow direction is desired, such as between 5° and 10°.

In a further embodiment of the preload device, the tube 162 described with reference to FIG. 7 may be replaced by a double lumen catheter having an internal lumen for return of the fluid to the bottom of the catheter (via pump 172) and an outer lumen provided with several openings along its length for removing air and fluid from the surrounding (via pump 168). By such a double lumen catheter, filling of the afterload device before use can easily be achieved and air removal during operation can be provided.

The afterload device may be accidentally filled with fluid if the heart becomes fibrillated, which should result in an alarm or other action via the load cell 74 described in FIG. 4. The same operation as the load cell may be achieved by other means, such as an optical sensor or a capacitive sensor, which senses the fluid level inside the afterload device.

The fluid used in evaluating the heart should be any suitable fluid having water as the basis. A suitable fluid is a modified Kreb's solution with added substances such as: albumin, another oncotic agent, erythrocytes, hormones, etc. Another example of a suitable fluid is disclosed in WO2009136838A1. It is also possible to use autologous blood, or a blood replacement solution.

The medium used for generating the counterpressure should have a density, which is several times lower than water, which normally means a gas. In addition, gas is compressible, which will provide the desired compliance. Thus, the medium should be a gas. The gas may be normal air or nitrogen gas or carbon dioxide gas. Since the gas may leak through the elastic tube into the fluid passing the heart, any gas which is detrimental to the heart should be avoided. In some embodiments, a heavier gas can be used, such as a noble gas, for example argon.

The evaluation and examination of the heart takes place outside the body, i.e. ex-vivo. However, a similar examination may be possible inside the body, while the heart is temporarily disconnected from the body circulation.

The exposition of the working heart to different temperature conditions can be examined by adjusting the temperature of the fluid in the heart and the temperature of the surrounding atmosphere of the heart.

The invention claimed is:

1. An afterload device for a beating heart during examination thereof, whereby the beating heart is provided with a fluid flow to a left or right atrium of the beating heart and the afterload device is connected to a left or right ventricle of the beating heart, the afterload device comprising:
   an inertia device comprising a tube configured for connection to a left or right ventricle of a beating heart and enclosing a volume of a fluid providing an inertia;
   a compliance device arranged after the tube of the inertia device and providing a compliance, the compliance device comprising a rigid body and a membrane tube arranged inside the rigid body for forming an annular space between the rigid body and the membrane tube defining a first medium volume, the membrane tube having an inner side and an outer side, the membrane tube being in contact with the fluid at the inner side of the membrane tube and the rigid body enclosing the first medium volume formed between the outer side of the membrane tube and the rigid body;
   a first restriction device arranged adjacent the compliance device and providing a fluid resistance to flow of the fluid, the first restriction device comprising a central plug and annular slits configured to be covered by the membrane tube at start of systole for providing a first resistance, and whereby the annular slits are uncovered during the systole for providing a second resistance, during a single heart beat; and
   a second restriction device having a first end and a second end, the second restriction device being connected at the first end to the first medium volume defined by the annular space between the rigid body and the membrane tube and at the second end to a second medium volume, for providing a medium flow resistance to flow of a medium from the first medium volume to the second medium volume.

2. The afterload device according to claim 1, further comprising:
   a backflow valve connected in parallel with the second restriction device and arranged to prevent flow from the first medium volume to the second medium volume and allow flow from the second medium volume to the first medium volume, whereby a pressure in the first medium volume will always be equal or larger than a pressure in the second medium volume.

3. The afterload device according to claim 2, wherein the medium is a compressible medium, and the pressure in the second medium volume is maintained at a pressure that corresponds to a desired systolic pressure.

4. The afterload device according to claim 1, wherein the first restriction device is a dynamic flow restriction device having the first resistance at low flow and the second resistance during high flow during one and the same heart beat, the first resistance being higher than the second resistance.

5. The afterload device according to claim 1, wherein the membrane tube is configured such that fluid provided by the beating heart during systole via the tube of the inertia device displaces the medium inside the annular space via the second restriction device to the second medium volume, whereupon a medium resistance is provided towards the flow of fluid during systole and a retrograde fluid flow is provided during diastole for providing coronary flow.

6. The afterload device according to claim 1, wherein the medium comprises one or more of air, nitrogen gas, carbon dioxide gas, argon, vapour or any combination thereof.

7. The afterload device according to claim 4, whereby an adjustable volume is connected to the first medium volume in order to form an adjustable compliance.

8. The afterload device according to claim 1, further comprising a valve configured for switching between a retrograde perfusion of an aorta of the beating heart and a normal perfusion of the aorta, the valve being connected to the afterload device at the tube of the inertia device.

9. The afterload device according to claim 5, further comprising vanes arranged adjacent an inlet of the annular space for keeping an entrance thereof open.

10. The afterload device according to claim 5, further comprising vanes arranged adjacent an outlet of the annular space for keeping an exit thereof open.

11. A circulation system comprising:
   (1) an afterload device for a beating heart during examination thereof, whereby the beating heart is provided with a fluid flow to a left or right atrium of the beating heart and the afterload device is connected to a left or right ventricle of the beating heart, the afterload device comprising:
      an inertia device comprising a tube configured for connection to a left or right ventricle of a beating heart and enclosing a volume of a fluid providing an inertia;
      a compliance device arranged after the tube of the inertia device and providing a compliance, the compliance device comprising a rigid body and a membrane tube arranged inside the rigid body for forming an annular space between the rigid body and the membrane tube defining a first medium volume, the membrane tube having an inner side and an outer side, the membrane tube being in contact with the fluid at the inner side of the membrane tube and the rigid body enclosing the first medium volume formed between the outer side of the membrane tube and the rigid body;

a first restriction device arranged adjacent the compliance device and providing a fluid resistance to flow of the fluid, the first restriction device comprising a central plug and annular slits configured to be covered by the membrane tube at start of systole for providing a first resistance, and whereby the annular slits are uncovered during the systole for providing a second resistance, during a single heart beat;

a second restriction device having a first end and a second end, the second restriction device being connected at the first end to the first medium volume defined by the annular space between the rigid body and the membrane tube and at the second end to a second medium volume, for providing a medium flow resistance to flow of a medium from the first medium volume to the second medium volume; and (2) a preload device configured to be used together with the afterload device during the examination of the beating heart, the preload device comprising a flexible and collapsible cylindrical tube that is arranged vertically, configured to be filled with fluid at a desired flow rate, and configured to be connected to a left or right atrium of the beating heart, whereby a fluid column is created in a portion of the cylindrical tube at a bottom of the cylindrical tube and whereby another portion of the cylindrical tube above the fluid column is collapsed, whereby an atmospheric pressure is generated above the fluid column, and whereby a predetermined load pressure is provided to fill the left or right atrium.

12. The circulation system according to claim 11, further comprising a de-aeration tube connected to a pump configured to remove possible air inside the flexible and collapsible cylindrical tube.

* * * * *